(12) United States Patent
Silver et al.

(10) Patent No.: US 10,013,779 B2
(45) Date of Patent: Jul. 3, 2018

(54) METAL ARTIFACT REDUCTION FOR 3D-DIGTIAL SUBTRACTION ANGIOGRAPHY

(71) Applicant: TOSHIBA MEDICAL SYSTEMS CORPORATION, Otawara (JP)

(72) Inventors: Michael D. Silver, Northbrook, IL (US); Satoru Ohishi, Otawara (JP); Yu-Bing Chang, Wheeling, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 116 days.

(21) Appl. No.: 14/746,012

(22) Filed: Jun. 22, 2015

(65) Prior Publication Data

US 2016/0371862 A1    Dec. 22, 2016

(51) Int. Cl.
| | |
|---|---|
| *G06K 9/00* | (2006.01) |
| *G06T 11/00* | (2006.01) |
| *A61B 6/00* | (2006.01) |
| *A61B 6/03* | (2006.01) |
| *G06T 7/33* | (2017.01) |
| *G06T 7/38* | (2017.01) |

(52) U.S. Cl.
CPC ............ *G06T 11/008* (2013.01); *A61B 6/032* (2013.01); *A61B 6/504* (2013.01); *A61B 6/5258* (2013.01); *G06T 7/337* (2017.01); *G06T 7/38* (2017.01); *G06T 11/005* (2013.01); *G06T 2207/10081* (2013.01); *G06T 2207/20221* (2013.01); *G06T 2207/20224* (2013.01); *G06T 2210/41* (2013.01); *G06T 2211/404* (2013.01)

(58) Field of Classification Search
CPC ........................................... G06T 2207/20221
See application file for complete search history.

(56) References Cited

U.S. PATENT DOCUMENTS

| | | | |
|---|---|---|---|
| 2011/0135177 A1* | 6/2011 | Ohishi | ............... A61B 6/481 382/130 |
| 2014/0133731 A1* | 5/2014 | Baumgart | ............. A61B 6/481 382/132 |
| 2014/0161331 A1* | 6/2014 | Cohen | .................... G06T 5/003 382/128 |

(Continued)

*Primary Examiner* — Oneal R Mistry
(74) *Attorney, Agent, or Firm* — Oblon, McClelland, Maier & Neustadt, L.L.P.

(57) ABSTRACT

A computed tomography (CT) imaging apparatus that reduces metal artifacts for digital subtraction angiography by, in circuitry, obtaining mask frames and contrast frames generated during scans of an object; performing a first reconstruction of the mask frames to generate metal volume data; identifying metal voxels in the metal volume data; re-projecting the metal voxels into the mask frames to generate metal-mask frames; defining a region of interest in each of the mask frames, each region of interest including metal regions; re-projecting the contrast frames; blending the mask frames with the re-projected contrast frames; registering the contrast frames with respect to the blended mask frames performing a cross-correlation analysis of the mask frames and the contrast frames, frame-pair-by-frame-pair; subtracting the registered contrast image from the corresponding mask image, frame-pair-by-frame-pair, to generate subtracted frames; and performing a second reconstruction on the subtracted frames.

20 Claims, 29 Drawing Sheets

(56) References Cited

U.S. PATENT DOCUMENTS

2015/0097833 A1* 4/2015 Razeto .................. G06T 7/0012
  345/424
2016/0242724 A1* 8/2016 Lavallee ................ A61B 6/032

* cited by examiner

F I G. 3B

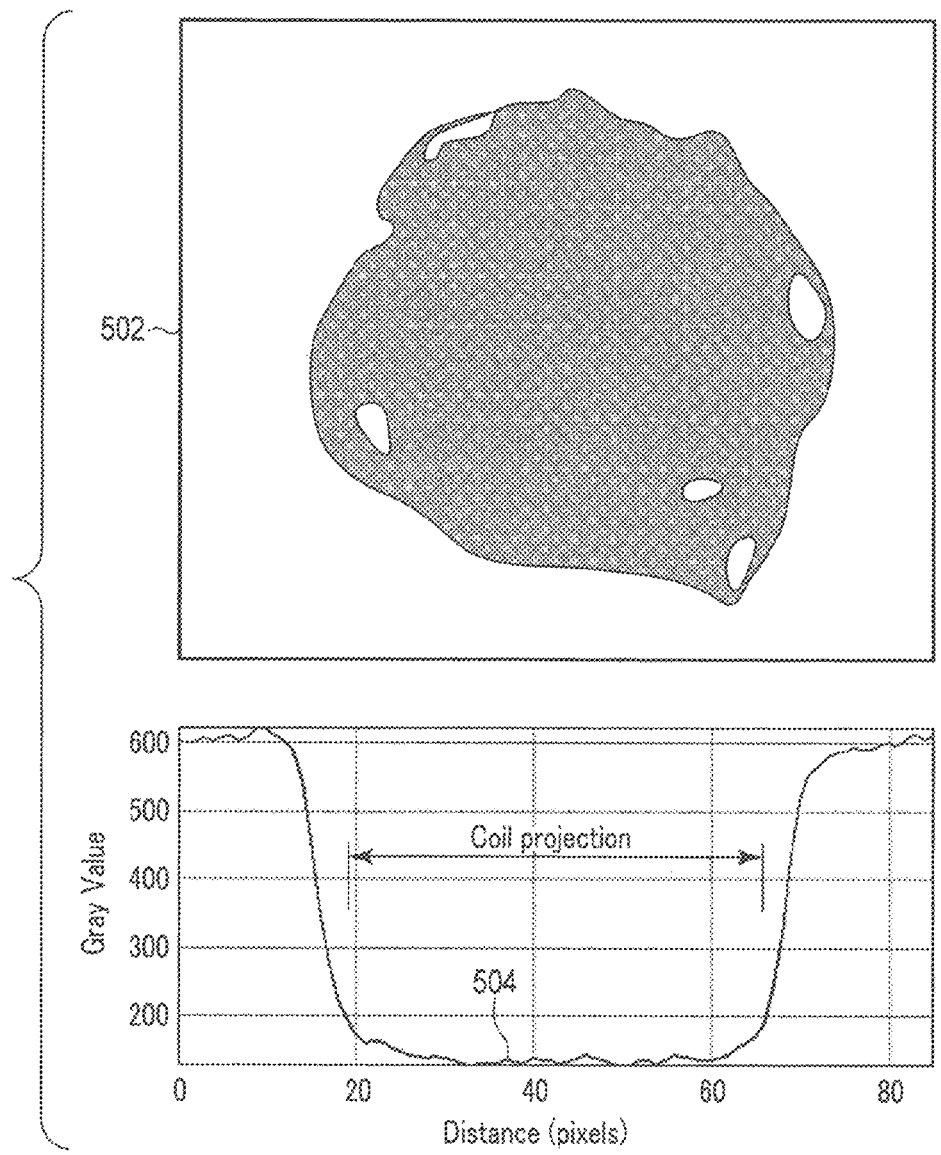
F I G. 5A

615

```
Subtract the mask frames from the registered
contrast frames to obtain difference images
614
          |
          v
Perform reconstruction on the difference
images to obtain metal-artifact-free images
616
```

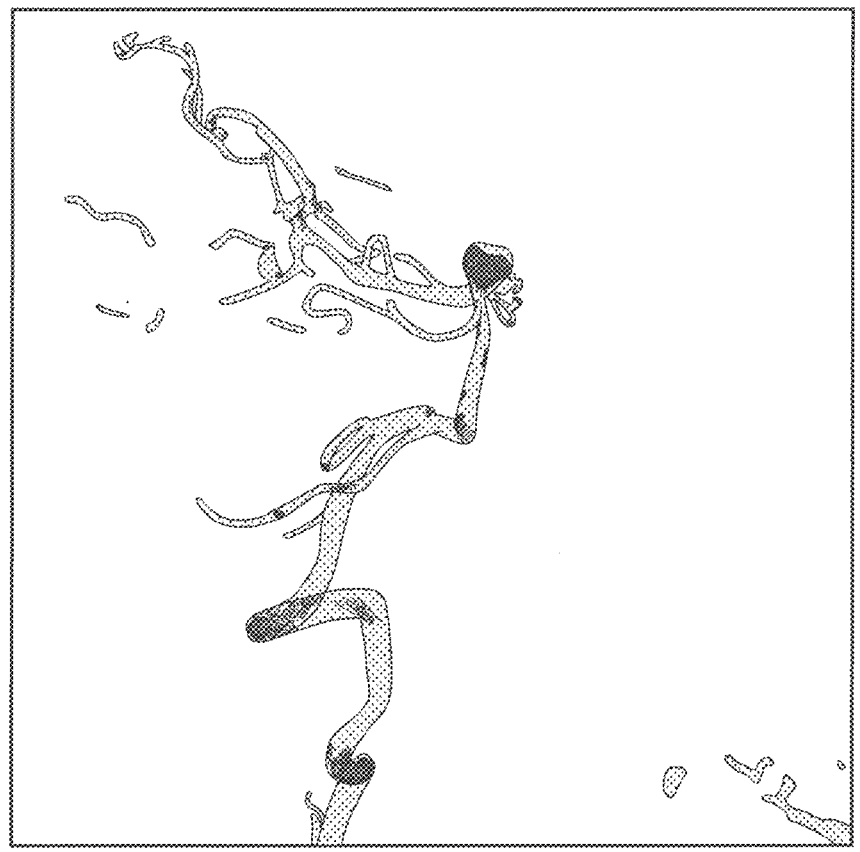
F I G. 7D

METAL ARTIFACT REDUCTION FOR 3D-DIGTIAL SUBTRACTION ANGIOGRAPHY

FIELD

The illustrative embodiments described herein relate to metal artifact reduction in CT-images reconstructed from a rotational sequence of digital subtraction angiography (DSA).

BACKGROUND

Digital Subtraction Angiography (DSA) imaging is used in interventional medicine to diagnose vascular disease or abnormality in patients to guide the intervention, and is used subsequent to treatment to document the effectiveness of treatment. DSA is a computer-aided image processing method used to enhance vasculature images in which each pixel of data acquired in an X-ray angiography procedure is digitized. DSA relies on the comparison between images taken immediately preceding an injection of a contrast bolus (mask frames) and those obtained as the contrast bolus is passing through the target vessels (contrast frames). The mask frames are digitally subtracted from the corresponding contrast frames resulting in the contrast-filled vessels being rendered on a display free of the background detail contained in the mask frames. Additional known image processing functions for further enhancing the final images are performed to produce a series of successive images, which are then replayed sequentially, enabling a healthcare practitioner to visualize fluid flow through the target vessels.

Often, a rotation sequence of sufficient rotational coverage is acquired of the mask and contrast frames so that computed tomographic (CT) reconstruction is possible. This enables the interventional team to see the target region in 3D without the problem of overlapping structures. However, if sufficient metal is in or near the target region, such as a coil, metal artifacts occur due to the highly attenuating nature of metal leading to no signal beneath the metal and also the very high frequency content of the metal that the imaging system cannot reliably render. The metal artifacts can be severe enough to render the value of the image of the target region useless. This invention is a method to greatly reduce (if not eliminate) the metal artifacts in such imaging systems and situations.

A key step in the metal artifact reduction (MAR) is to pixel-shift a contrast frame relative to the mask (or reference) frame to align the pair of frames to match backgrounds. This also can aid the visualization of the contrast-enhanced structures in DSA images even without the CT-reconstruction. This process of translating and/or rotating the mask frames to account for movement and changes in the contrast frames is referred to as registration. In some cases, artifacts arise in processing multiple individual frames if one or more individual frames exhibit shifts in contrast-enhanced structures in a different direction than that of the background.

BRIEF DESCRIPTION OF THE DRAWINGS

A more complete appreciation of the disclosed inventions and the many attendant advantages thereof will be readily obtained as the same becomes better understood by reference to the following detailed description when considered in connection with the accompanying drawings, wherein:

FIG. 3B shows an example of a contrast frame;

FIG. 5A shows an example of the mask frame with only coil projections;

FIG. 7D shows an example of a re-projected contrast frame;

DETAILED DESCRIPTION

Figure 1:
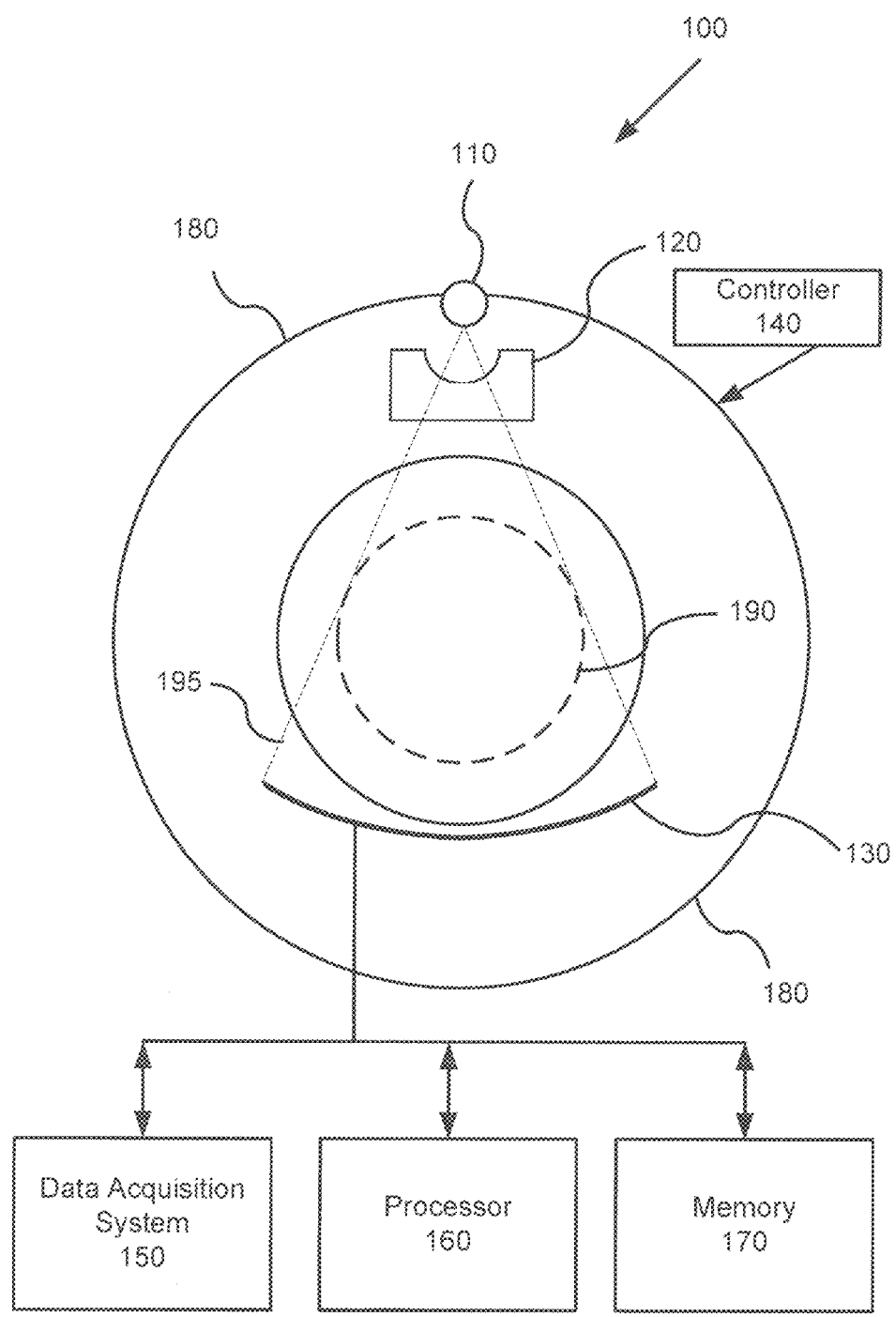
FIG. 1 shows a schematic diagram of one implementation of a CT-scanner having a single X-ray source and a single detector unit.

In one embodiment, there is provided a computed tomography (CT) imaging apparatus that reduces metal artifacts in CT reconstructed images of digital subtraction angiography, the CT imagining apparatus comprising processing circuitry configured to (1) obtain a plurality of mask frames and a plurality of contrast frames generated during scans of an object; (2) perform a first reconstruction of the mask frames to generate metal volume data; (3) identify metal voxels in the mask volume data; (4) re-project the metal voxels to generate metal-mask frames representing absorption due to metal objects; (5) define a region of interest in each of the mask frames using the metal-mask frames to identify metal regions, and each region of interest includes metal regions; (6) generate contrast frames by reconstructing a contrast image using the contrast frames, identify voxels in the contrast image corresponding to contrast agent, and re-projecting the identified voxels to obtain re-projected contrast frames; (7) blend the mask frames with the re-projected contrast frames; (8) register the metal-mask frames with the contrast frames by performing a cross-correlation analysis of the mask frames and the contrast frames, frame-pair-by-frame-pair, using the defined region of interest in each of the mask frames; (9) subtract the registered mask frame from a corresponding contrast frame, frame-pair-by-frame-pair to generate subtracted frames; and (10) perform a second reconstruction on the subtracted frames to generate a metal-artifact-free image.

In another embodiment, there is provided a computed tomography (CT) imaging apparatus that reduces metal artifacts in digital subtraction angiography, the CT imagining apparatus comprising processing circuitry configured to (1) obtain a plurality of mask frames and a plurality of contrast frames generated during scans of an object; (2) perform a first reconstruction of the mask frames to generate metal volume data; (3) identify metal voxels in the mask volume data; (4) define a region of interest in each of the mask frames, each region of interest including metal regions; (5) perform an image-wise judgment function to determine whether to register all of the mask and the contrast frames; (6) re-project the metal voxels to generate metal-mask frames representing absorption due to metal objects; (7) define a region of interest in each of the mask frames using the metal-mask frames to identify metal regions, and each region of interest includes metal regions; (8) perform an frame-wise judgment function to determine whether to register the single pair of mask and the contrast frames; (9) generate contrast frames by reconstructing a contrast image using the contrast frames, identify voxels in the contrast image corresponding to contrast agent, and re-projecting the identified voxels to obtain re-projected contrast frames; (10) blend the mask frames with the re-projected contrast frames; (11) register the metal-mask frames with the contrast frames by performing a cross-correlation analysis of the mask frames and the contrast frames, frame-pair-by-frame-pair, using the defined region of interest in each of the mask frames; (12) subtract the registered mask frame from a corresponding contrast frame, frame-pair-by-frame-pair to generate subtracted frames; and (13) perform a second reconstruction on the subtracted frames to generate a metal-artifact-free image.

In another embodiment, there is provided a computed tomography (CT) imaging apparatus to improve registration and reduce artifacts in digital subtraction computed tomography, the apparatus including processing circuitry configured to (1) obtain mask frames and contrast frames generated during scans of an object, each mask frame and contrast frame at a respective projection angle of a plurality of projection angles; (2) subtract each mask frame from the corresponding contrast frame generating difference frames; (3) reconstruct a first contrast image using the difference frames; (4) project the first contrast image at the plurality of projection angles to generate contrast re-projection frames; (5) blend each mask frame with the corresponding contrast re-projection frame generating blended mask frames; (6) register each contrast frame with the corresponding blended mask frame to align absorption features of the contrast frame with absorption features of the blended mask using a transformation that includes a translation; (7) subtract each mask frame from the corresponding contrast frame after the mask frame and the contrast frame are aligned using the transformation generating subtracted frames; and (8) reconstruct a second contrast image using the subtracted frames.

In another embodiment, there is provided a computed tomography (CT) imaging apparatus to improve registration and reduce artifacts in digital subtraction computed tomography, the apparatus including processing circuitry configured to (1) obtain pre-mask frames and contrast frames generated during scans of an object, each pre-mask frame and contrast frame at a respective projection angle of a plurality of projection angles; (2) reconstruct a mask image using the pre-mask frames; (3) identify metal voxels in the mask image; (4) re-project the metal voxels at the plurality of projection angles generating mask frames; (5) define a plurality of regions of interest in the mask frames corresponding to regions within the mask frames including metal absorption features; (6) subtract each mask frame from the corresponding contrast frame generating difference frames; (7) reconstruct a first contrast image using the difference frames; (8) project the first contrast image at the plurality of projection angles to generate contrast re-projection frames; (9) blend each mask frame with the corresponding contrast re-projection frame generating blended mask frames; (10) register each contrast frame with the corresponding blended mask frame to align absorption features of the contrast frame with absorption features of the blended mask within the corresponding regions of interest and using a transformation that includes a translation and a rotation, wherein the transformation corresponds to a maximum value of a cross-correlation between the blended mask frame and the corresponding contrast frame; (11) subtract each mask frame from the corresponding contrast frame after the mask frame and the contrast frame are aligned using the transformation generating subtracted frames; and (12) reconstruct a second contrast image using the subtracted frames.

CT images can be reconstructed from projection data (frames) taken from a rotational sequence of projection angles. For example, two-dimensional frames of projection data representing the attenuation through a three-dimensional object can be used to reconstruct a three-dimensional image of the object, when the frames correspond to an adequate span of projection angles (e.g., 180° plus the fan angle). For clarity, the discussion herein adheres to the convention that the reconstructed three-dimensional images are each referred to as "images," whereas the two-dimensional projection data is generally referred to as "frames" rather than images in order to differentiate the "frames" (i.e., projection images) from the CT reconstructed "images." In particular, "contrast frame" refers to projection data, whereas "contrast image" refers to a CT reconstructed image.

Similar to three-dimensional CT imaging, CT imaging can also be performed on two-dimensional slices, wherein one-dimensional frames of projection data can be used to reconstruct a two-dimensional image of the object. The discussion herein focuses predominantly on the example of three-dimensional CT imaging. However, one of ordinary skill will recognize that the methods discussed herein are also applicable to the case of two-dimensional CT imaging.

FIG. 1 illustrates a simplified schematic structure of a CT apparatus 100 that includes a detector array to detect transmitted photons. Aspects of this disclosure are not restricted to a CT apparatus 100 as the medical imaging system. In particular, the structures and procedures described herein can be applied to other medical imaging systems, and the descriptions provided herein specifically relating to a CT apparatus 100 and the detection of photons should be considered as illustrative.

A detector array, a photon detector, and/or a photon detector array may be referred to herein merely as a detector. The CT apparatus 100 illustrated in FIG. 1 includes an X-ray tube 110, filters and collimators 120, and a detector 130. In one implementation, the detector 130 can be an array of energy integrating detector elements arranged in a third-generation geometry. In one implementation, the CT apparatus 100 also includes energy-discriminating (e.g., photon-counting) detectors sparsely arranged in a fourth-generation geometry, and the energy-discriminating detectors are arranged along a radius different from the radius along which the detector 130 is arranged. The CT apparatus 100 also includes additional mechanical and electrical components such as a gantry motor and a controller 140 to control the rotation of the gantry, control the X-ray source, and control a patient bed. The CT apparatus 100 also includes a data acquisition system 150 and processing circuitry 160. The processing circuitry 160 is configured or programmed to generate CT images based on the projection (view) data acquired by the data acquisition system. For example, the processing circuitry 160 includes a reconstruction part that reconstructs spectral CT images. The processing circuitry is programmed to perform methods and execute algorithms in accordance with the processes, equations, and relationships described herein. The processing circuitry and data acquisition system can make use of a memory 170, which is configured to store, e.g., data obtained from the detector, and reconstructed images.

The X-ray tube 110, filters and collimators 120, detector 130, and controller 140 can be provided in a frame 180 that includes a bore. The frame 180 has a general cylindrical or donut shape. In the view shown in FIG. 1, a longitudinal axis of the bore of the frame 180 is in the center of the bore and extends into and out of the page. An interior of the bore, identified as area 190, is a field-of-view (FOV) of the CT apparatus 100. An object to be scanned, such as a patient, is placed in the target area with, e.g., a patient table. The object can then be irradiated by the X-ray tube 110 with a fan or cone of radiation 195. The processing circuitry 160 is programmed to determine photon counts of captured incident X-ray photons. The data acquisition system 150, the processing circuitry 160, and the memory 170 can be implemented as a single machine or computer, or as separate machines or computers that are coupled together or distributed via a network or other data communication systems. The controller 140 can also be coupled via the network or other data communication system, and can be implemented by a separate machine or computer, or as part of another machine or computer of the system.

In FIG. 1, the detector 130 is a rotational detector array that rotates with the X-ray tube 110 with respect to the longitudinal axis. Although not shown in FIG. 1, a stationary detector array can also be included, thus providing a rotating detector array and a stationary array, together, in the frame 180. Other detectors can be implemented. p In one implementation, the frame 180 of the CT apparatus 100 is a radiography gantry. The processing circuitry 160 can include reconstruction processing circuitry, image processing circuitry, and pre-processing circuitry, wherein the term "circuitry" can be interpreted as a Central Processing Unit (CPU) executing program instructions or as special-purpose hardware circuitry, such as an FPGA, or other specialized circuitry.

Figure 2:
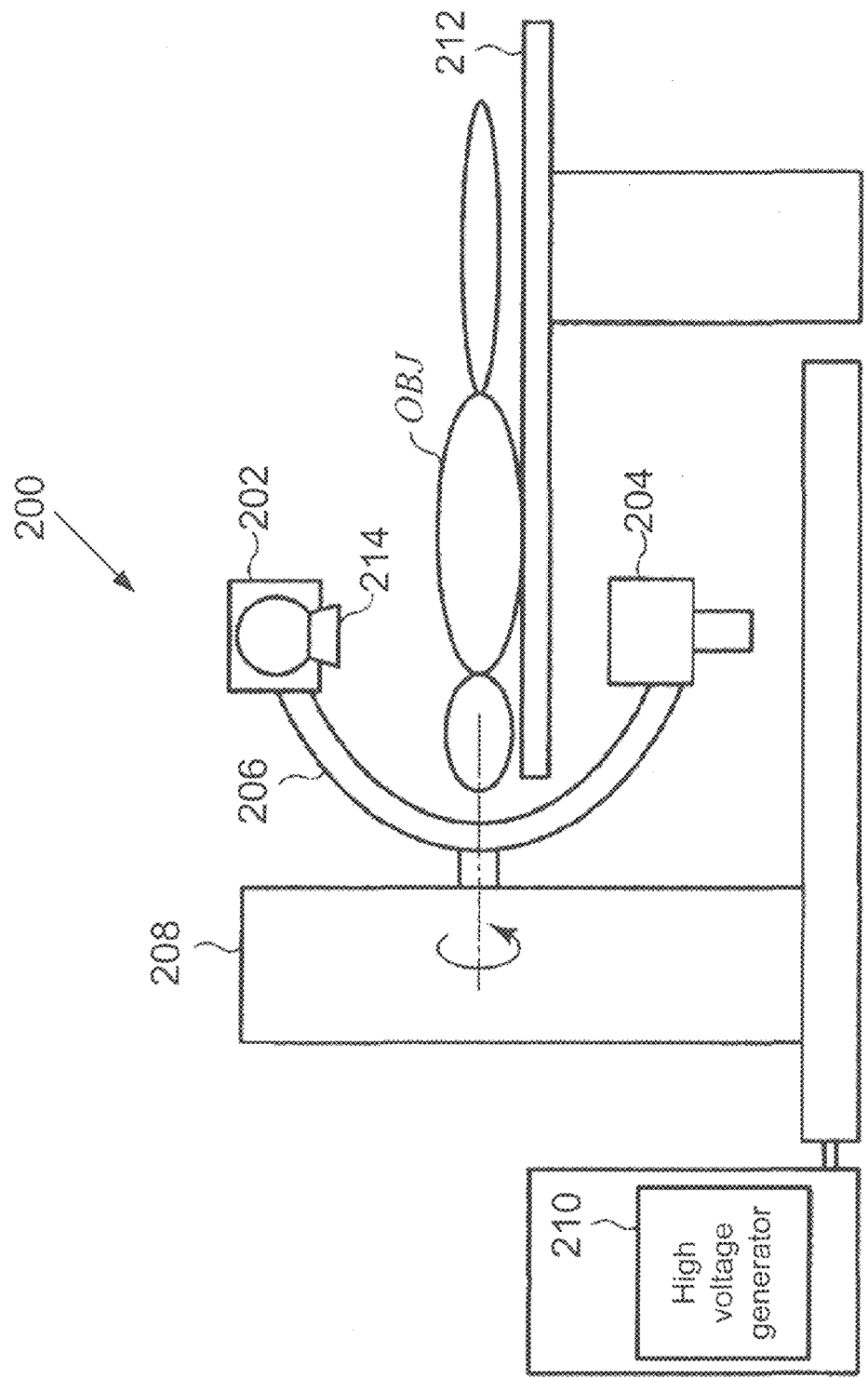
FIG. 2 shows a schematic diagram of one implementation of a CT-scanner using a C-arm configuration.

FIG. 2 shows an example of a CT apparatus 100 or radiography gantry, wherein the apparatus uses a C-arm configuration. As shown in FIG. 2, the CT apparatus 200 includes an X-ray tube 202, X-ray detector 204, C-arm 206, stand 208, high-voltage generator 210, bed 212, and X-ray stop device 214.

The high-voltage generator 210 generates a high voltage to be applied between the electrodes of the X-ray tube 202, and also generates a filament current to be supplied to the cathode filament of the X-ray tube 202. Upon receiving the high voltage and filament current, the X-ray tube 202 generates X-rays. The X-ray stop device 214 shapes X-rays generated by the X-ray tube 202. The X-ray detector 204 can be a two-dimensional array of a plurality of detection elements (pixels) that directly or indirectly convert incident X-rays into electric charges. The X-ray tube 202 is mounted on, for example, one end of the floor type C-arm 306. The X-ray detector 204 is mounted on the other end of the C-arm 206. The X-ray detector 204 faces the X-ray tube 202 through an object OBJ to be examined which is placed on the bed 212. The C-arm 206 is rotatably supported on the stand 208. Repeating radiography with respect to the object OBJ while rotating the C-arm 206 makes it possible to acquire X-ray frames (projection data) in many directions which are required for three-dimensional image reconstruction.

Radiography control circuitry controls the rotation of the C-arm 206, the application of high voltages from the high-voltage generator 210 to the X-ray tube 202, and reading of signals from the X-ray detector 204 in order to execute rotational radiography and generate X-ray projection data.

In Digital Subtraction Angiography (DSA), with a fixed viewing angle, a contrast frame is subtracted from a non-contrast mask frame to obtain blood vessel data and eliminate the background of other soft tissues and bone information. In one implementation of 3D DSA with C-arm gantries, the gantry undergoes two scans, each scan spanning projection angles of 180° plus the fan angle of the beam (other implementations can also be realized where the span of the projection angles is either greater than or less than 180° degrees plus the fan angle of the beam). One scan is performed without the contrast agent and the other scan is performed with contrast agent. The non-contrast image frames are subtracted from the contrast image frames, frame-by-frame. If enough frames are acquired to span the required projection angles, then the subtracted frames can be processed via computed tomography methods into a 3D image volume of the vasculature. This method of obtaining difference image frames for a plurality of scan angles and reconstructing an image from the difference frames is not limited to the case of a gantry having a C-arm geometry and using half-scan reconstruction methods. Other CT-apparatus geometries and other short-scan and full-scan reconstruction methods can also be used.

Clinical applications often involve the implantation of metal, such as coils or stents, into the patient. Coils, which are often closely packed into aneurysms and are of high density, cause severe streaks in CT reconstructions. In 3D-DSA, ideally there is no motion of the patient between the mask and contrast frames, and the metal subtracts out exactly so that a reconstruction with good image quality is possible. However, in clinical practice, once injection starts, patients can feel discomfort (e.g., some patients feel a burning pain as the contrast agents flows into their cerebral arteries). Thus, patients are likely to move even though they are told to stay still. As a result of the patient's movement, the subtraction between the mask frames and the contrast frames results in large negative and positive values in the difference frame. In particular, negative and positive values will result at opposite edges of the metal due to the subtraction of the larger absorption due to the metal from the small absorption of the soft matter and vice versa at the other boundary of the metal. Thus, these offsets result in residual metal artifacts in the difference image. Removing metal artifacts from DSA CT-reconstructed acquisitions caused by incomplete subtraction of the metal due to the motion of the patient is a challenge in CT image reconstruction.

The process of translating and rotating the mask frame (or contrast frame) to compensate for movement and changes between the mask and contrast frames is called registration, or alternatively referred to as registering the frames. In one implementation, registration can be performed by selecting of region of interest (ROI) within the frames corresponding to a significant feature (e.g., a metallic stent or coil) that is independent of the contrast agent. The region of interest (ROI) is compared between the two frames and one frame is adjusted relative to the other frame (e.g., the mask frame is translated and rotated relative to the contrast frame or vice versa) until the significant feature is observed to be overlapped and aligned between the two frames. In one implementation, the overlap and alignment between the two frames is optimized by maximizing a cross-correlation between the ROI of the two frames.

When the absorption features corresponding to the contrast agent are in close proximity to, and of similar absorption magnitude to, the absorption due to the significant feature (e.g., metallic stent or coil), then using the cross-correlation to register the frames can cause bias in the registration process, resulting in an offset caused by the registration process. To correct for this bias, a blended mask frame can be used for registration rather than the original mask frame. The blended mask frame has a similar absorption texture to the contrast frame, and the greater similarity between the blended mask frame and the contrast frame improves the ability to obtain the optimal overlap between the frames using the cross-correlation function. Colloquially speaking, comparing the blended mask frame with the contrast frame creates more of an apples-to-apples comparison. To create the blended mask frame, a mask frame is combined with a re-projection frame of the contrast agent. Then the blended mask frame and contrast frame are aligned to each other during the registration process. Once the contrast frames have been registered with respect to the blended mask frames, then difference frames can be obtained by taking the difference frame-by-frame between the mask frames and the registered contrast frames. Finally, a DSA image can be reconstructed using the difference frames and a CT image reconstruction method. For example, a half-scan reconstruction method can be used if the difference frames span projection angles of 180° plus the fan angle. Another reconstruction method, such as iterative reconstruction using TV regularization or various short-scan methods, can be used if the difference frames span a different angle of the projection angles.

Figure 3A:
FIG. 3A shows an example of a mask frame.
Figure 3C:
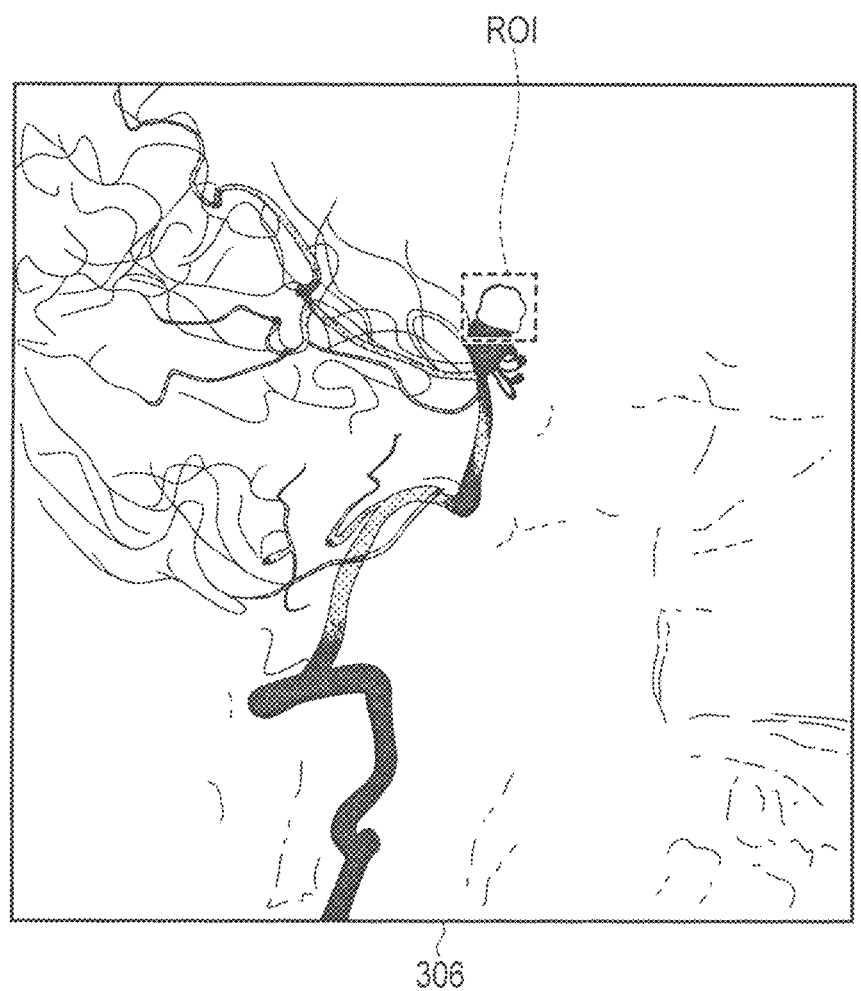
FIG. 3C shows an example of a subtraction frame.

FIG. 3A illustrates an example of a mask frame 302. The ROI is defined to include a metal coil. FIG. 3B illustrates an example of a contrast frame 304. Comparing FIG. 3B to FIG. 3A, the change in absorption of certain vasculature structure is clearly visible. FIG. 3C illustrates an example of a subtraction frame 306. Subtraction is performed after the logarithm has been taken of the measured X-ray intensity for the mask and contrast frames. Alternatively, subtraction can also be performed by dividing the mask and contrast intensities and then taking the logarithm of the ratios. The subtraction frame 306 is generated by subtracting the mask frame 302 from the contrast frame 304. The subtraction frame makes the vasculature structure more visible by subtracting off the background. However, the alignment between the mask frame and the contrast frame is imperfect, resulting in a residual artifact from the metal coil. The subtraction frame illustrates a misalignment of coil projections between the mask and the contrast frame due to improper registration between the mask and the contrast frame.

Figure 3D:
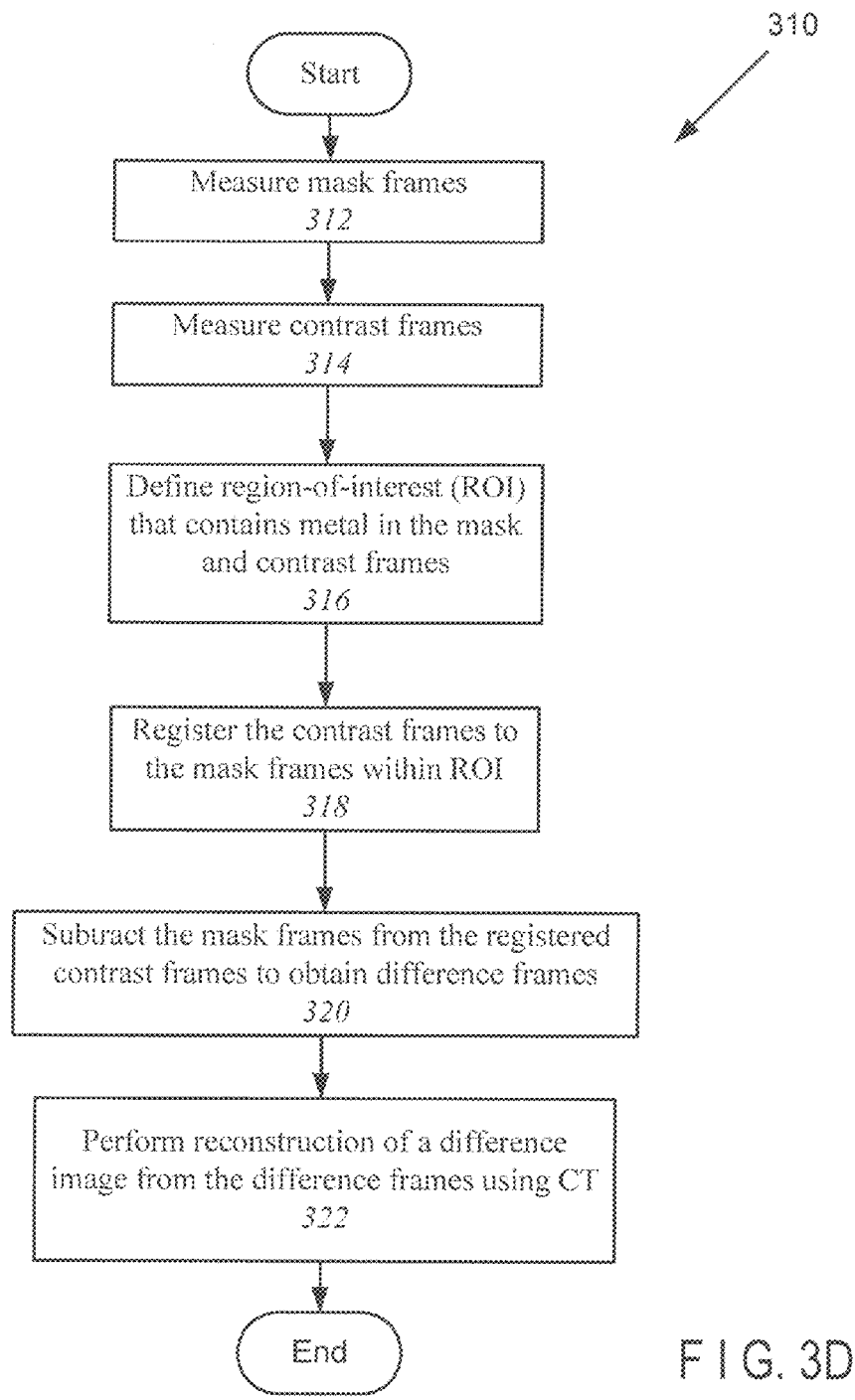
FIG. 3D is a flow diagram of one implementation of a method of processing mask and contrast frames to reconstruct a contrast image.

FIG. 3D shows a flow diagram of a method 310 resulting in improper registration between the mask and the contrast frame. In step 312 of method 310, the mask frames are measured. In step 314 of method 310, the contrast frames are measured. Next, in step 314 a ROI is defined. Then at step 318, the contrast frames are registered to the mask frames by maximizing the cross-correlation between the respective contrast and mask frames. Difference frames are calculated frame-by-frame from the respective registered contrast frames and mask frames, at step 320. Finally, at step 322, a difference frame is reconstructed from the difference frames using a CT image reconstruction method. For example, the CT image reconstruction method can be a filtered-backprojection method such as the Feldkamp method, or an iterative reconstruction method such as the algebraic reconstruction technique or the total variation (TV) minimization method.

Figure 4A:
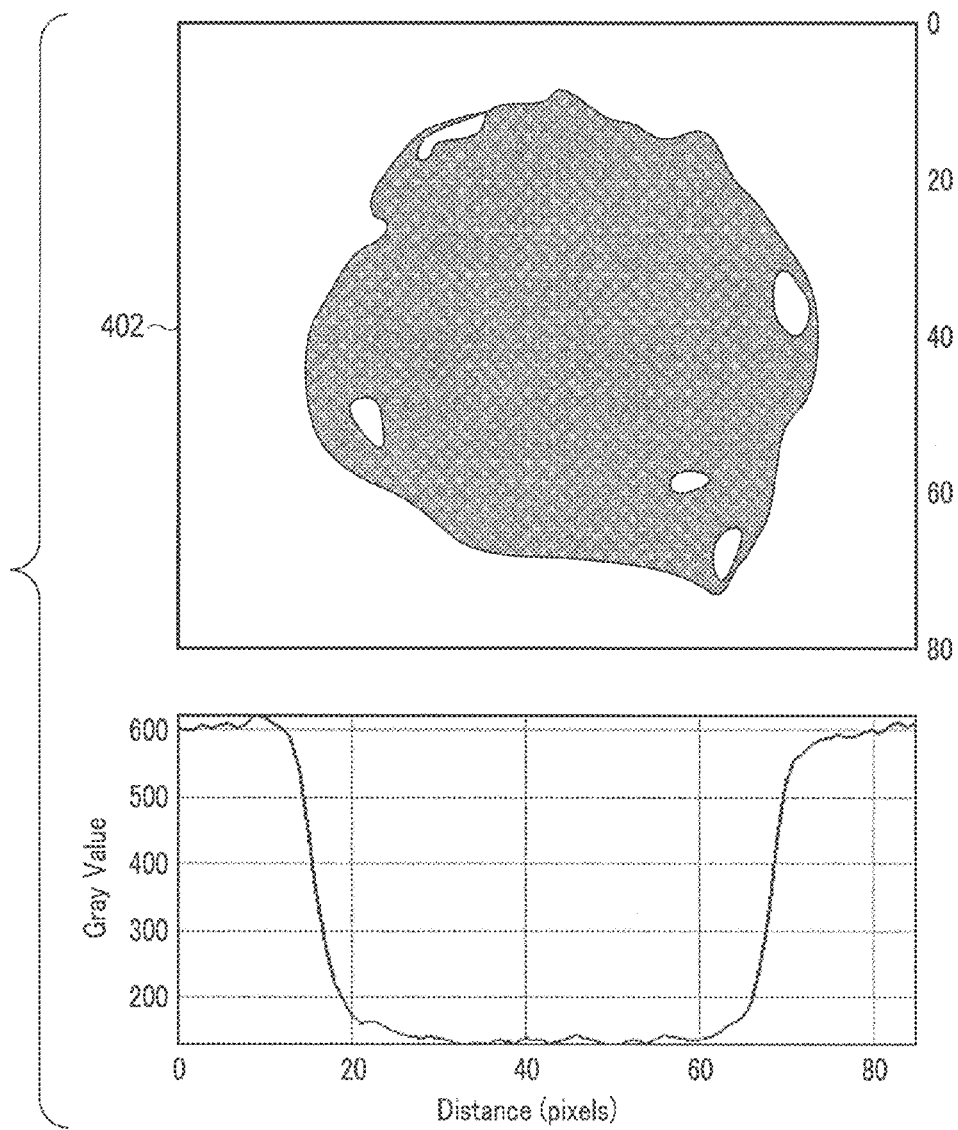
FIG. 4A shows an example of the mask frame in a region of interest (ROI)
Figure 4B:
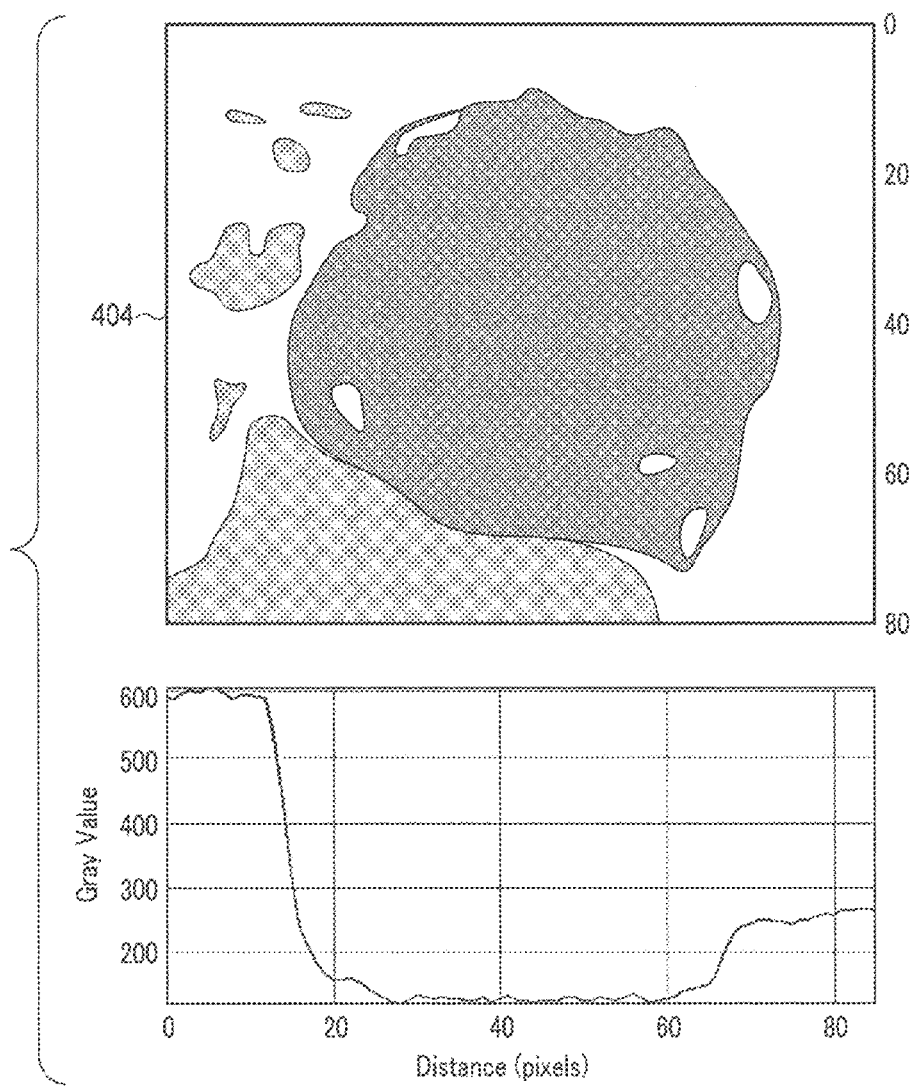
FIG. 4B shows an example of the contrast frame in an ROI.
Figure 4C:
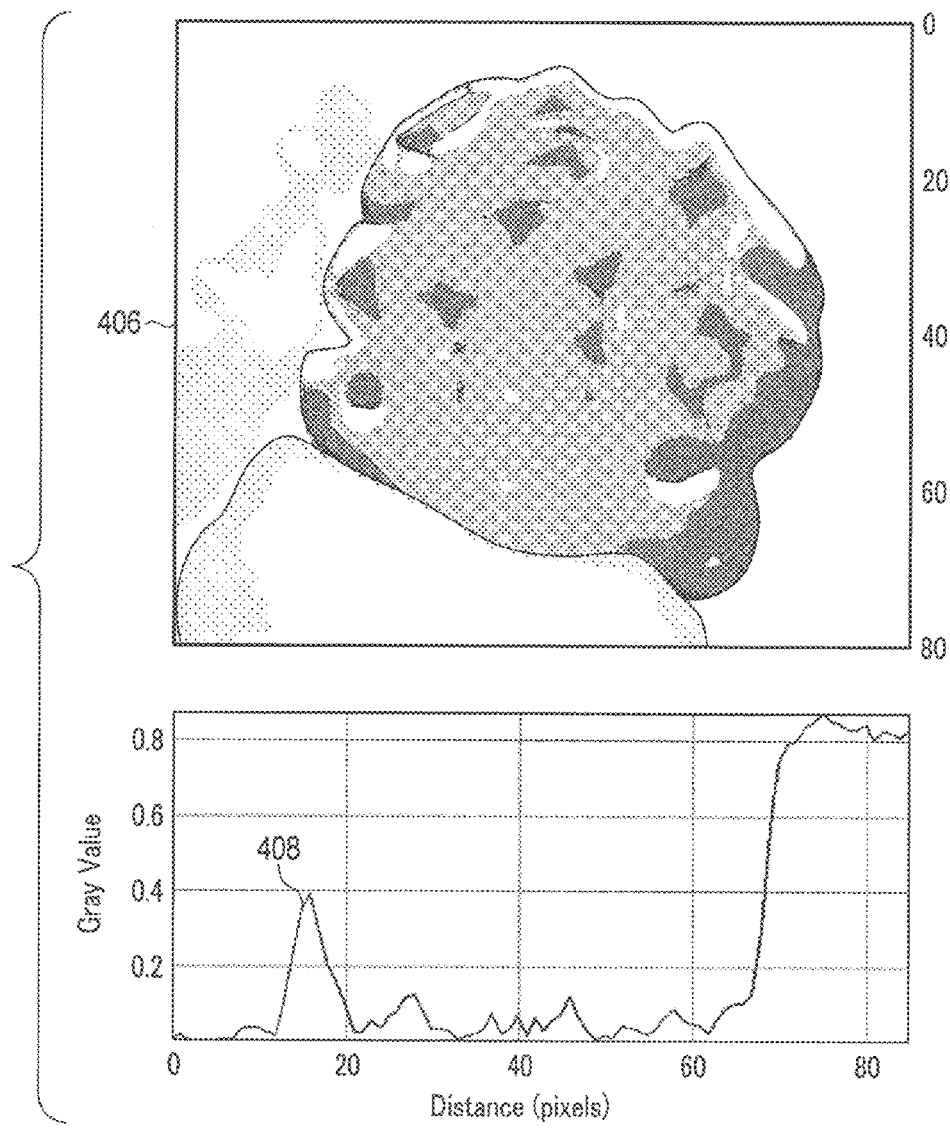
FIG. 4C shows an example of the subtraction frame in an ROI.

The mask frame, contrast frame, and the subtraction frame can be represented as a matrix of pixels with each pixel having a numeric value representing the attenuation of X rays through the object along a path from the x-ray source to the pixel and rendered as a shade of gray. FIG. 4A illustrates an example of the mask frame near the coil projections 402, wherein the lineout plot below the greyscale plot shows a one-dimensional plot of the greyscale values (e.g., higher number corresponds to more white (transmission) through the patient) along a vertical crosssection of the mask frame. FIG. 4B illustrates an example of the contrast frame near the coil projections 404. FIG. 4C illustrates an example of the subtraction frame 406. A peak 408 in the subtraction frame 406 indicates the subtraction does not cancel out the coil projection. For example, due to movement of the patient, the metal in the contrast frame is shifted down and to the right-hand side of the contrast frame. Therefore, when the mask frame is subtracted from the contrast frame the upper-right portion of the metal image is not fully subtracted out of the difference frame creating the bright halo seen in FIG. 4C, and on the bottom-right of the metal image the difference between mask and contrast frames results in values that are too low (e.g., zero or negative values). The process of correcting for displacements of mask and contrast frames is called registration and can minimize the residual artifacts such as the halo on the upper-left of the metal region and the dark patch on the bottom-right o of the metal region shown in FIG. 4C.

Registration can be performed by translating and rotating the relative positions of the mask frame and the contrast frame in order to maximize a cross-correlation between the mask frame and the contrast frame. For many projection frames, maximizing the cross-correlation is sufficient to register the contrast frame with respect to the mask frame, or to register the mask frame with respect to the contrast frame. However, when the absorption due to the contrast agent is similar to the absorption due to the metal coil or stent and the contrast agent comes into close proximity with the metal coil or stent, then using the cross-correlation to register the respective frames can result in bias.

For example, the metal in the mask frame after registration could be shifted towards the centroid between the combined absorption of the metal and the contrast agent in the contrast frame. For example, where the absorption due to the contrast agent is mostly below a metal coil, as in FIGS. 4A-C, the centroid of the metal together with the contrast agent is lower than the centroid of the metal absorption by itself. Thus, the cross-correlation function will be offset causing the metal absorption image in the mask frame to be skewed to partial overlap contrast agent in the contrast frame. Thus, registration between the mask and contrast frames can result in the mask frame being offset downwards relative to the contrast frame. One consequence of this offset is exemplified by the difference frame having a residual metal artifact 408, as shown in the lineout of FIG. 4C.

Figure 5B:
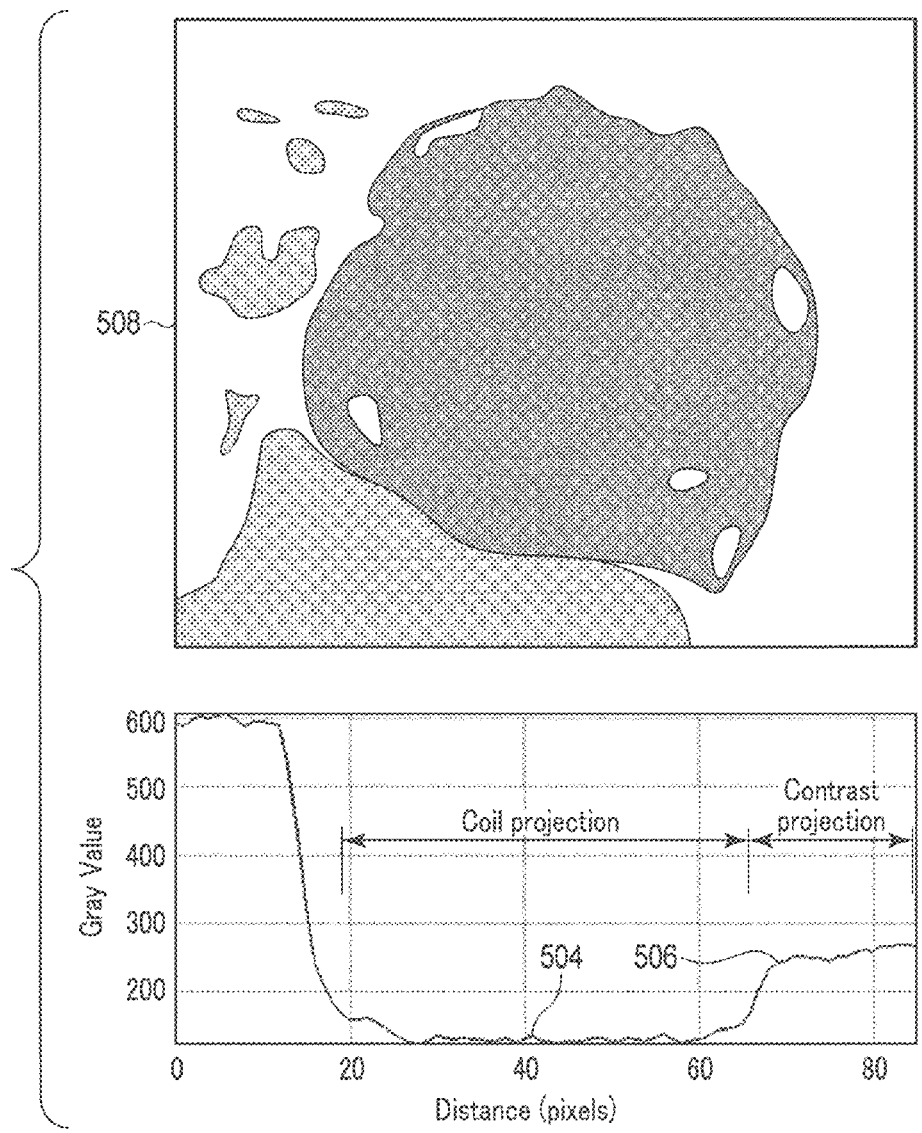
FIG. 5B shows an example of the contrast frame with both the coil projections and contrast projections.

FIGS. 5A and 5B show that the mask frame 502 includes only coil projection 504 while the contrast frame 506 includes coil projection 504 in combination with a contrast projection 508 representing the absorption due to a contrast agent. Therefore, the absorption centroid of the mask frame can be different from the absorption centroid of the contrast frame, which can introduce bias during registration of the mask and contrast frames. Further, FIG. 5B shows that the magnitude of absorption due to the coil is of the same order of magnitude as the absorption due to the contrast agent. Thus, the cross-correlation registration between mask and contrast frames can be biased.

To remedy the bias in the registration, blended mask frames can be used for registration in place of the mask frames. As explained below, the blended mask frames can be obtained by combining the mask frames with re-projections of the contrast frame, wherein the contrast frame is the CT reconstructed image from the difference frames. Using blended mask frames for registration results in contrast image being reconstructed from difference images twice— the first reconstruction occurs before the blended-mask registration in order to generate the re-projection contrast frames that are blended with the mask frame to create the blended mask, and the second reconstruction occurs after the blended-mask registration in order to reconstruct the final three-dimensional contrast image. For the first reconstruction of the contrast image, registration is performed using conventional methods (e.g., without a blended mask). The resultant contrast image reconstructed from the difference frames is then further processed to obtain the re-projected contrast frames.

In one implementation, noise and artifacts, such as the metal artifacts shown, e.g., in FIG. 4C can be suppressed in the re-projected contrast frames by using a threshold and a region-growing method to identify aberrant voxels in the contrast image, and then segmenting out these voxels of the contrast agent from the re-projection step. Region growing is a straightforward region-based image segmentation method. It is also classified as a pixel-based image segmentation method since it involves the selection of initial seed points. This approach to segmentation examines neighboring pixels of initial seed points and determines whether the pixel neighbors should be added to the region. The process is iterated on, in the same manner as general data-clustering algorithms. For example, the seed points can be determined using a thresholding method, and the determination of the pixel/voxel neighbors to add to the region can be determined using, e.g., the connectivity between a seed and other pixels, the descending order of pixel intensities, and thresholds to decide if the neighboring pixels are included in the image cluster.

For example, metals are known to have larger absorption coefficients than soft matter such as blood vessels, muscle, water, and even bone. Thus, a predetermined absorption threshold between typical soft matter absorption and metal absorption can be used to distinguish voxels likely to correspond to metal. For example, the pre-determined threshold for a metal image can be 4000 Hounsfield units, so that voxels with absorption greater than this threshold are determined to be metal voxels. These metal voxels can be flagged as aberrant and excluded from re-projection.

Additionally, voxels corresponding to negative absorption would also be aberrant and can be excluded from re-projection. One of ordinary skill will recognize that different threshold ranges can be used to either segment out or segment in voxels of the contrast image according to pre-determined absorption ranges. Additionally, in a CT apparatus using dual-energy CT and/or photon-counting detectors, the spectral variation in X-ray absorption for each voxel can also be used as indicia differentiating between various voxel types (e.g., metal, soft matter, and contrast agent), and this additional indicia can also be used in the decision process to determine whether a voxel should be segmented in or segmented out of the contrast re-projection.

In one implementation, a contrast projection mask can be created using a priori knowledge of the contrast agent or other information regarding the contrast image. Using a pixel driven re-projection method, a binary mask can be generated, wherein a value of one (true) means that a pixel/voxel is likely to include contrast agent and a value of zero (false) means that a pixel/voxel is not likely to include contrast agent. In one implementation, in the contrast image, voxels corresponding to the contrast agent can be segmented in using a threshold and a region-growing method. A contrast projection mask can then be created by projecting the segmented-in voxels onto a projection frame, wherein pixels of the frame corresponding to projections including a pre-determined number of segmented in voxels are given a value of one (true). Otherwise the pixels of the contrast projection mask frame are given a value of zero (false). One example of a contrast re-projection mask is shown in FIG. 7C and the corresponding contrast re-projection frame is shown in FIG. 7D. The contrast re-projection mask is used to mask the re-projection process wherein the contrast re-projection frames are created by reprojecting the three-dimensional contrast image.

In one implementation, the resolution of the contrast re-projection frames can be less than the full resolution of the final difference frames used to reconstruct the final 3D-DSA image. A purpose of the contrast re-projection frames is to superimpose the gross structure of the contrast agent in the contrast frames into the mask frames to create the blended mask frames. These blended mask frames satisfy their purpose for improving registration even when the contrast re-projection frames have only coarse resolution. Therefore, a high level of resolution is not required for the re-projection contrast frames, and thus the initial contrast image also is not required to have finer resolution. Further, decreasing the resolution for the initial contrast image and re-projection contrast frames decreases the computational burden on the method 600. For example, if the matrices of the final reconstructed images are 512×512×512, then the matrices of the first reconstructed three-dimensional contrast image can be 128×128×128 or smaller.

After obtaining the blended mask frames, the contrast frames can be registered relative to the blended mask frames (upsampling and interpolation can be used to make the blended mask size equal to the contrast frames if smaller matrices were used for the initial contrast image and the re-projection contrast frames). After registration is performed, the mask frames are subtracted from the registered contrast frames to create subtracted frames. Then CT reconstruction is performed using the subtracted frames, and this second reconstruction can be performed with finer resolution (e.g., to generate a 512×512×512 image) for the final contrast image without metal artifacts due to the improved registration enabled by the blended mask frames. Because the registration prior to the second CT reconstruction of the contrast image was performed using the blended mask frames, the bias should be removed from the registration process and the final contrast image should be free from the metal artifacts present in the initial contrast image.

Referring now to FIG. 6, a flowchart 600 is shown describing one implementation of a method performed by processing circuitry for removing the indications of metal artifacts from 3D-DSA CT reconstructed acquisitions caused by incomplete subtraction of the metal due to the motion of the patient.

In step 602, the processing circuitry generates mask volume data by performing a first reconstruction using mask frames. The mask frames are obtained during a scan without contrast agent injected into the patient. Three-dimensional images are reconstructed with smaller matrices in the first reconstruction than the matrices of the final reconstructed images. Smaller matrices used in the first reconstruction can be equal to or less than a quarter of the final reconstruction images. For example, if the matrices of the final reconstructed images are 512×512×512, then the matrices of the first reconstructed three-dimensional contrast images are 128×128×128 or smaller. Furthermore, a morphological filter of dilation can be used to make sure all metal data are identified.

In step 604, the processing circuitry identifies metal voxels by thresholding out all voxel values above a predetermined user threshold from the mask frame. The predetermined threshold is a value that can create the best differentiation between soft matter and metal. In one implementation, 4000 HU is applied based on the acquisition protocols.

In step 606, the processing circuitry re-projects the metal voxels into the metal frames to generate mask frames, frame-pair-by-frame-pair. The processing circuitry performs a forward re-projection of metal voxels from the mask volume data from the image domain to the projection domain.

In step 608, the processing circuitry defines the ROI that contains metal pixels in both the mask frames and the contrast frames.

Process 617 is a method to generate re-projected contrast frames. The steps of process 617 are shown in FIG. 6B.

In step 618 of process 617, the processing circuitry subtracts the mask frames from the corresponding contrast frames to obtain DSA frames.

In step 620 of process 617, the processing circuitry performs a reconstruction on the obtained DSA frames.

In step 622 of process 617, the processing circuitry identifies contrast voxels by thresholding out all voxels above a predetermined user threshold from the reconstructed 3D-DSA image.

In step 624 of process 617, the processing circuitry generates a binary contrast projection mask by designating a pixel to have a value one when the corresponding re-projection ray passes through a predetermined number of voxels corresponding to contrast voxels. Further, a pixel is designated to a value of zero when the corresponding re-projection ray passes through less than the predetermined number of voxels corresponding to contrast voxels. This re-projection process can be referred to as "pixel-driven" re-projection.

In step 626, the processing circuitry re-projects the segmented contrast voxels corresponding to contrast agent in the 3D-DSA image to obtain re-projected contrast frames indicative of the absorption at each pixel due to the contrast image. This re-projection process can be referred to as "ray-driven" re-projection. In one implementation, the re-projection contrast frame is the product of the "pixel-driven" re-projection creating a binary contrast mask and the "ray-driven" re-projection of contrast image onto a binary contrast mask. No re-projection is performed outside the binary contrast projection mask because regions outside the binary contrast projection mask correspond to regions that theoretically sum to zero during the mask subtraction process. Therefore, excluding those regions outside the binary contrast projection mask from the re-projection process reduces noise contributions from imperfect cancelation those regions. In one implementation, the re-projection contrast frame is the "ray-driven" re-projection.

Figure 8:
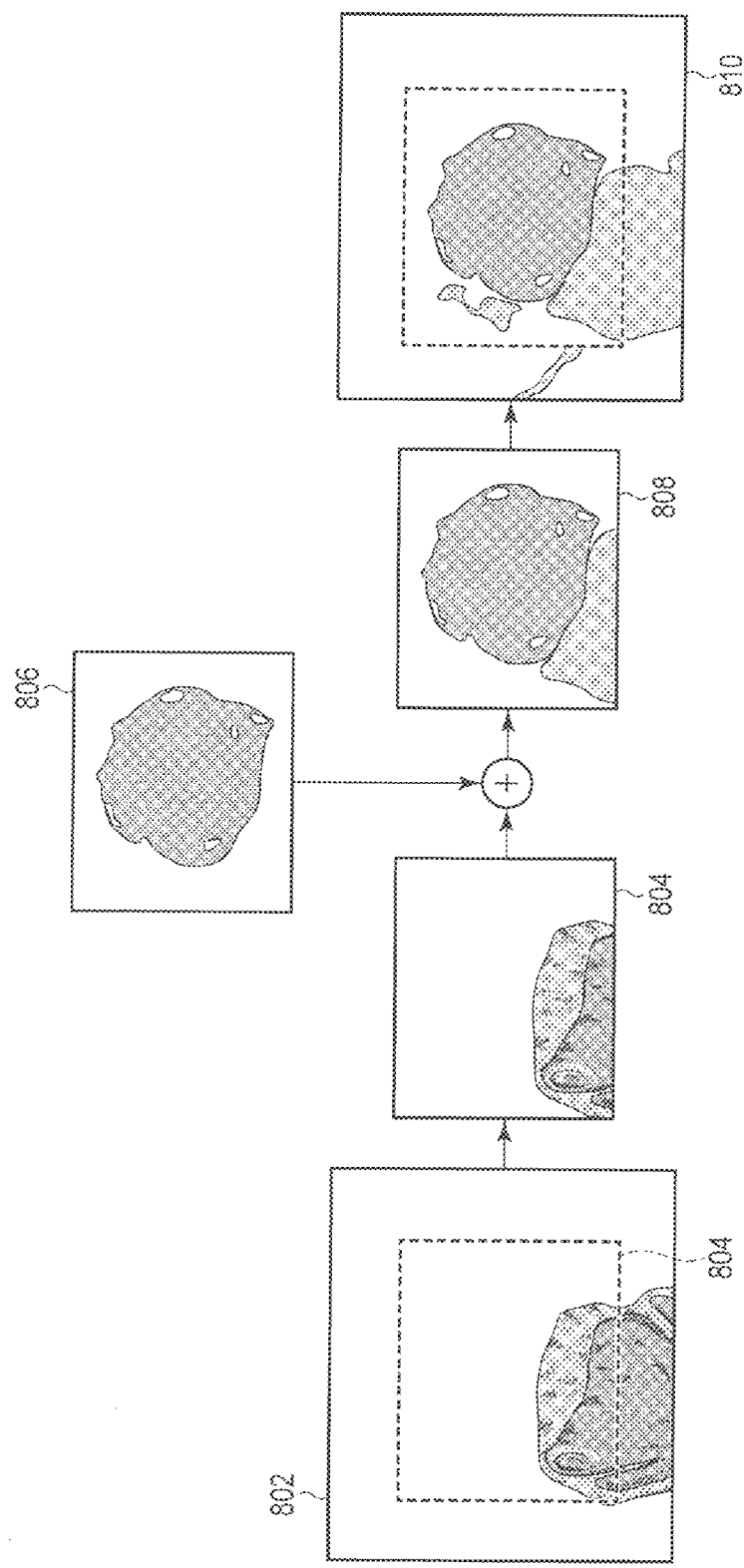
FIG. 8 shows an illustrative procedure of re-projecting the contrast frame.

In step 610, the mask frames are blended with the contrast re-projection frames to create blended mask frames. FIG. 8 shows one implementation of generating the blended mask frames from the mask frames and the contrast re-projection frames.

In step 612, the contrast frames are registered to the blended mask frames. In one implementation, registration is performed by maximizing a cross-correlation between the contrast frames and the blended mask frames within the ROI.

In process 615, metal-artifact-free contrast images are generated using the difference frames between the registered contrast frames and the mask frames to perform CT image reconstruction. As shown in FIG. 6C, process 615 begins with step 614, wherein the difference frames are determined by calculating the frame-by-frame difference between the registered contrast frames and the mask frames.

In step 616, the metal-artifact-free contrast images are reconstructed from the difference frames using any known CT image reconstruction method. Where only half-scans (i.e., a scan spanning projection angles of 180° plus the fan angle) has been performed for the mask and contrast frames, a half-scan CT reconstruction method is used.

Figure 6A:
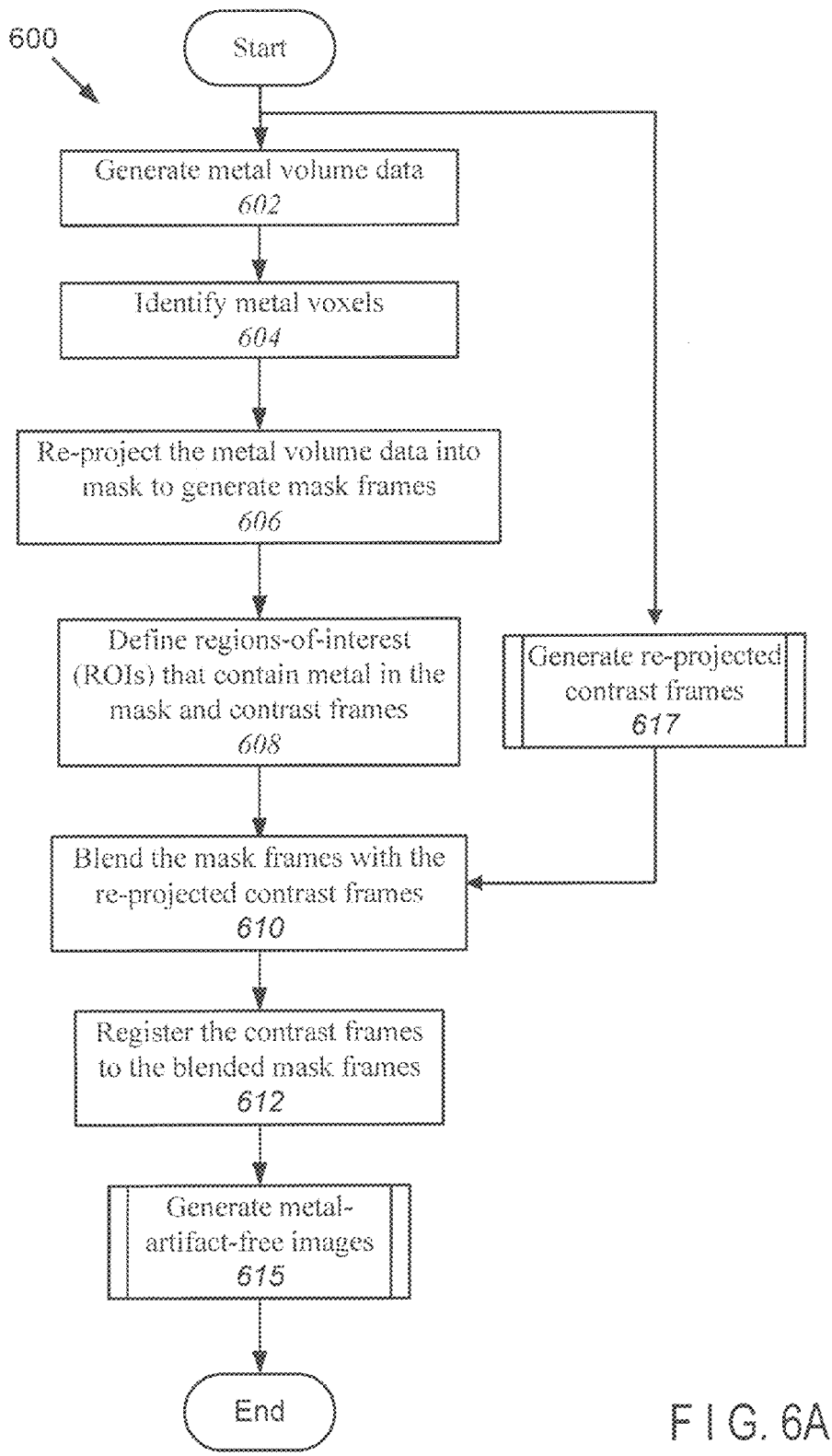
FIG. 6A shows a flow diagram of one implementation of a metal artifact reduction method.
Figure 6B:
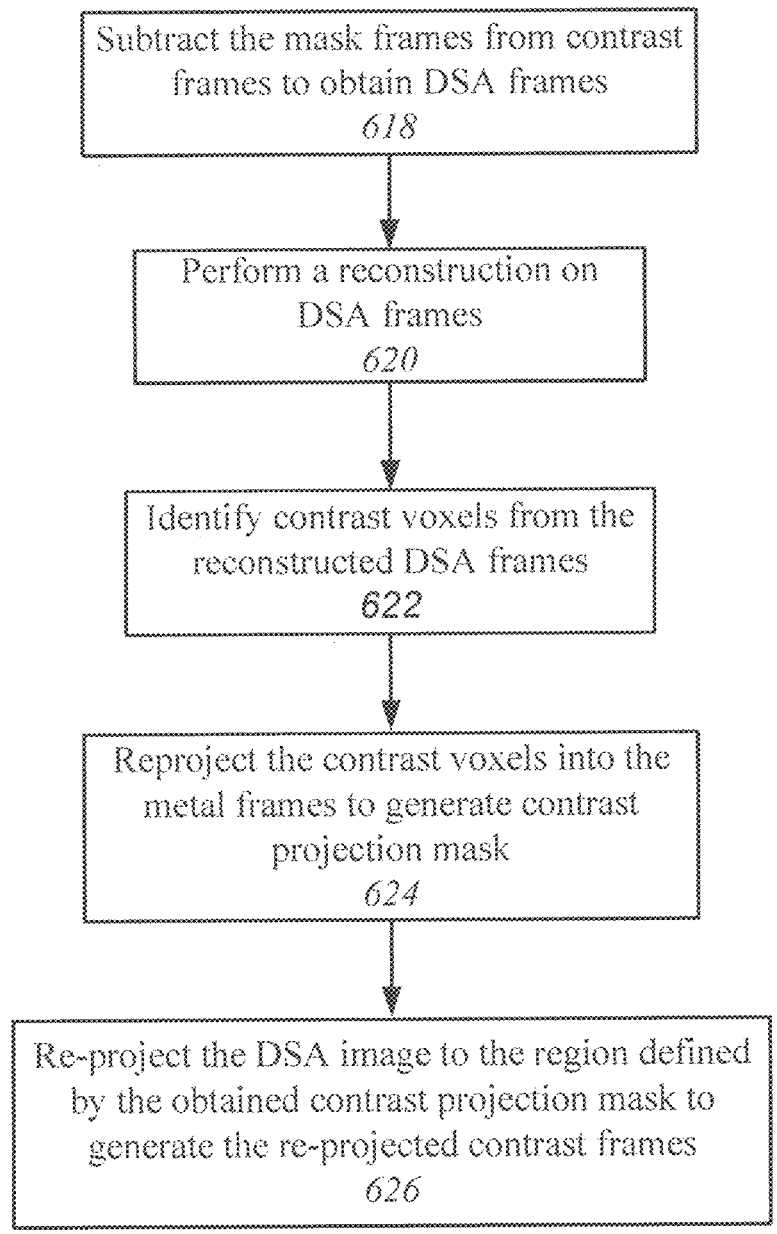
FIG. 6B shows a flow diagram of one implementation of a process to generate re-projected contrast frames.
Figures 6C, 7A:
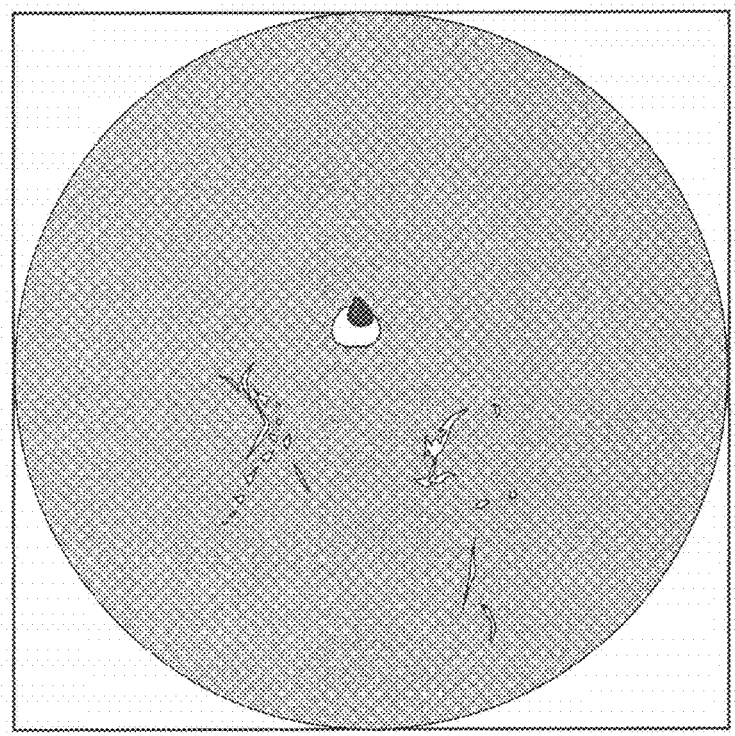
FIG. 6C shows a flow diagram of one implementation of a process to reconstruct a difference frame corresponding to a difference between a mask and a contrast frame.
FIG. 7A shows an example of a slice of a 3D-DSA image, in which CT reconstruction has been performed using the contrast frames.
Figure 7B:
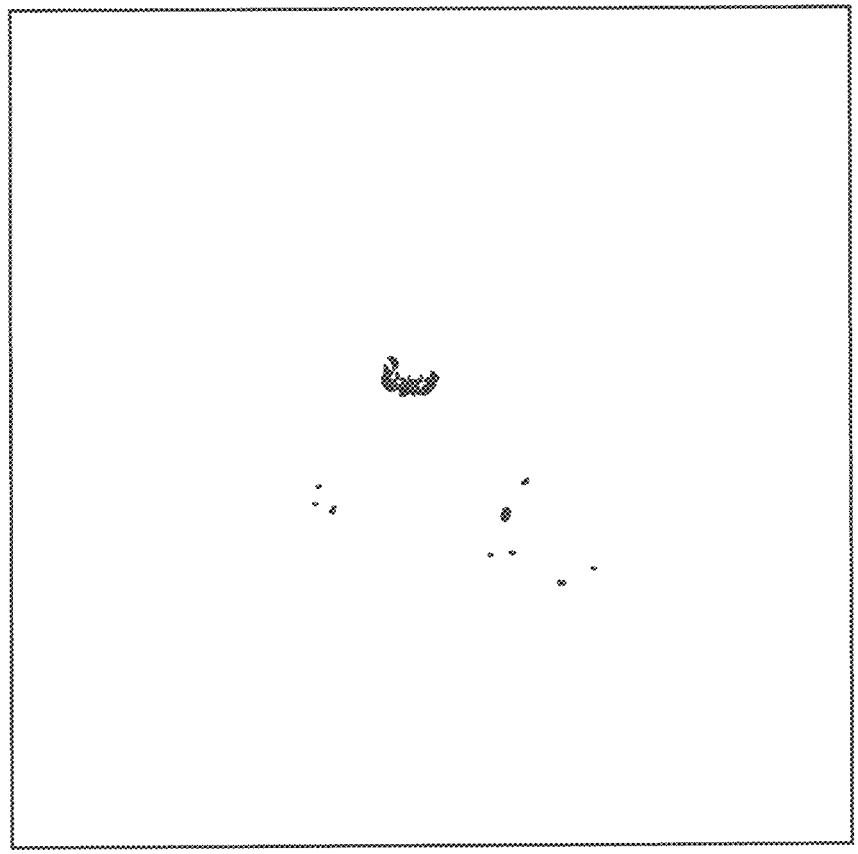
FIG. 7B shows an example of a mask for the contrast frames.
Figure 7C:
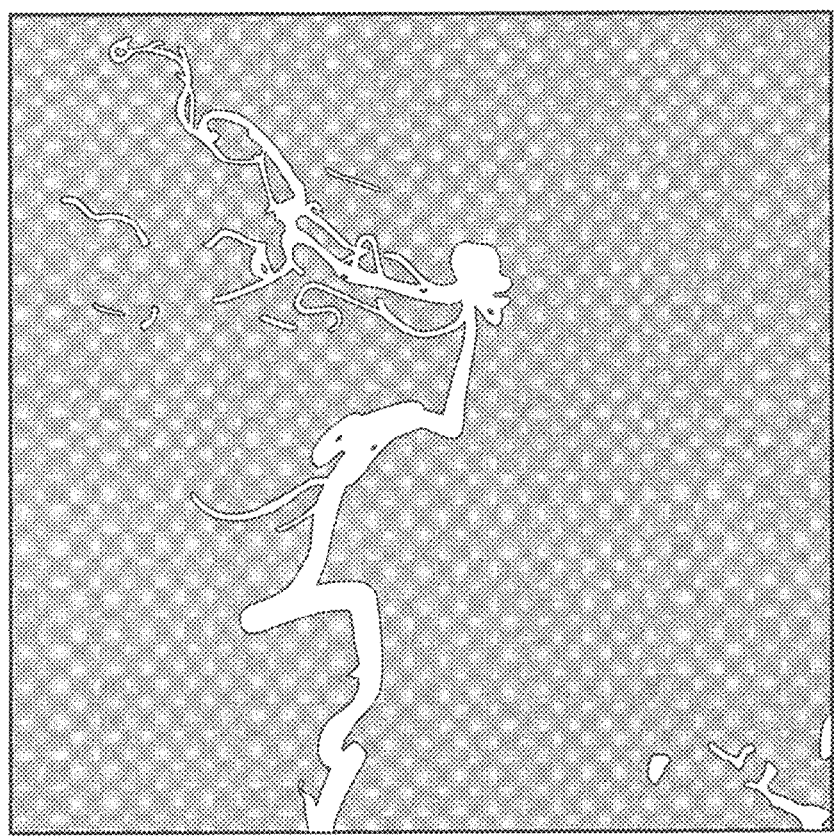
FIG. 7C shows an example of a contrast projection mask.

FIG. 7A is an example of a cross-section through a 3D-DSA image. FIG. 7B is an example of a mask for the contrast images segmenting out aberrant voxels. FIG. 7C is an example of the contrast projection mask segmenting in the contrast image. FIG. 7D is an example of the re-projected contrast frames. These re-projected contrast frames can be blended with the mask frames to create the blended mask frames.

In step 610 of FIG. 6A, the processing circuitry blends the mask frames with the re-projected contrast frames to generate blended contrast frames.

Figure 9A:
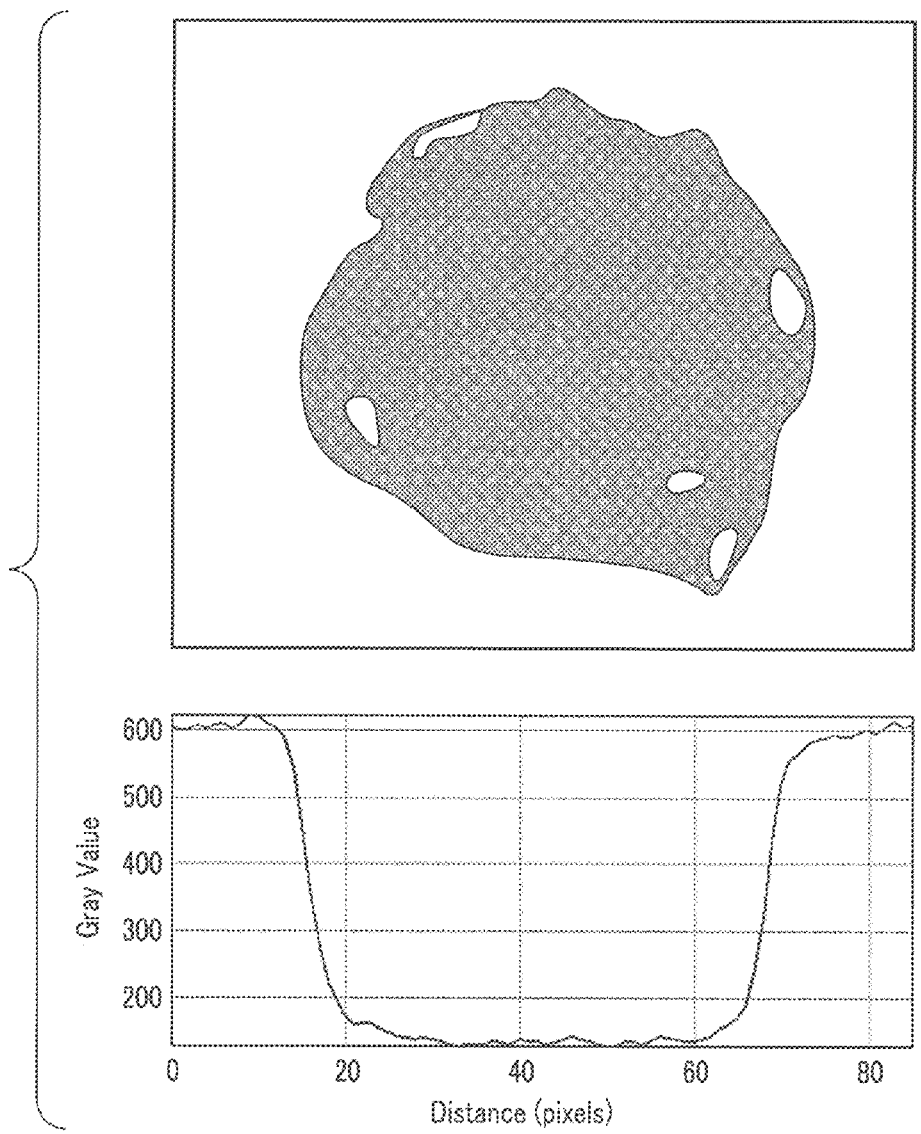
FIG. 9A shows an example of the mask frame.
Figure 9B:
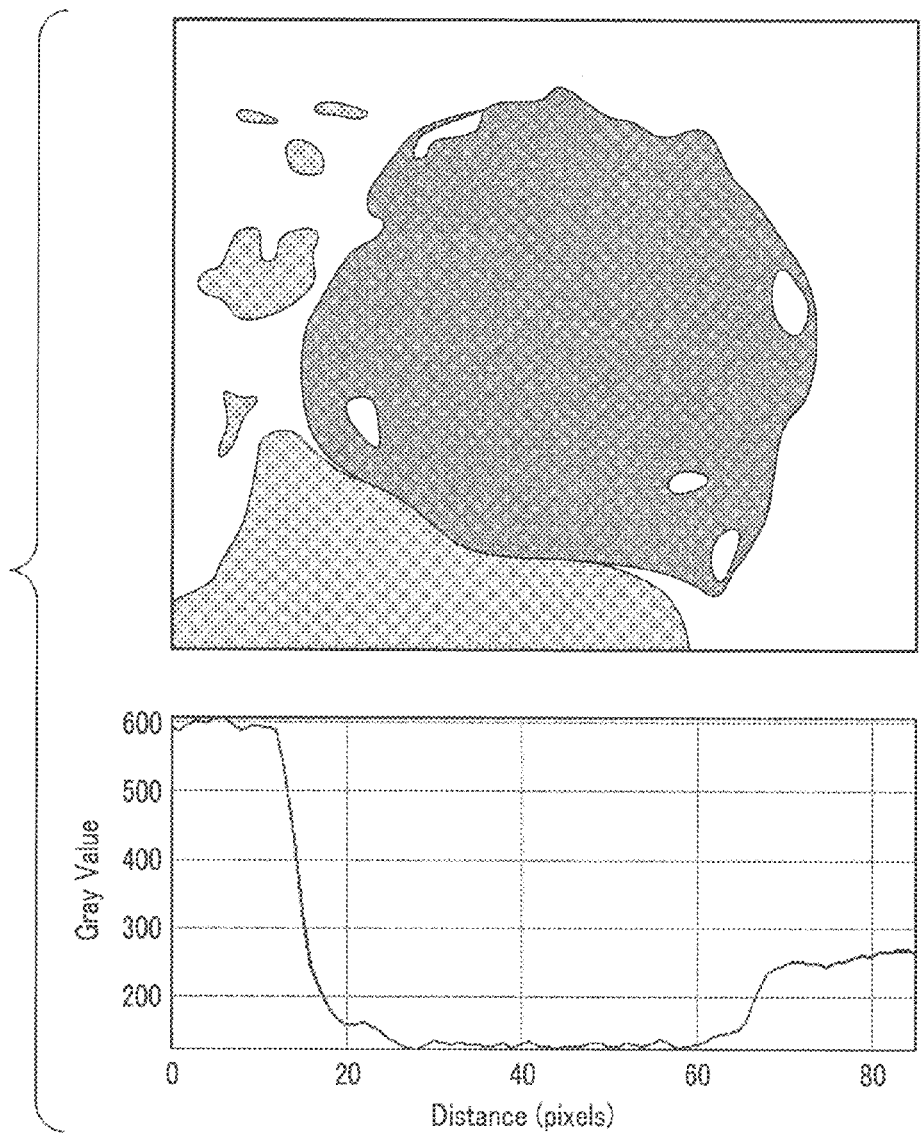
FIG. 9B shows an example of the contrast frame.
Figure 9C:
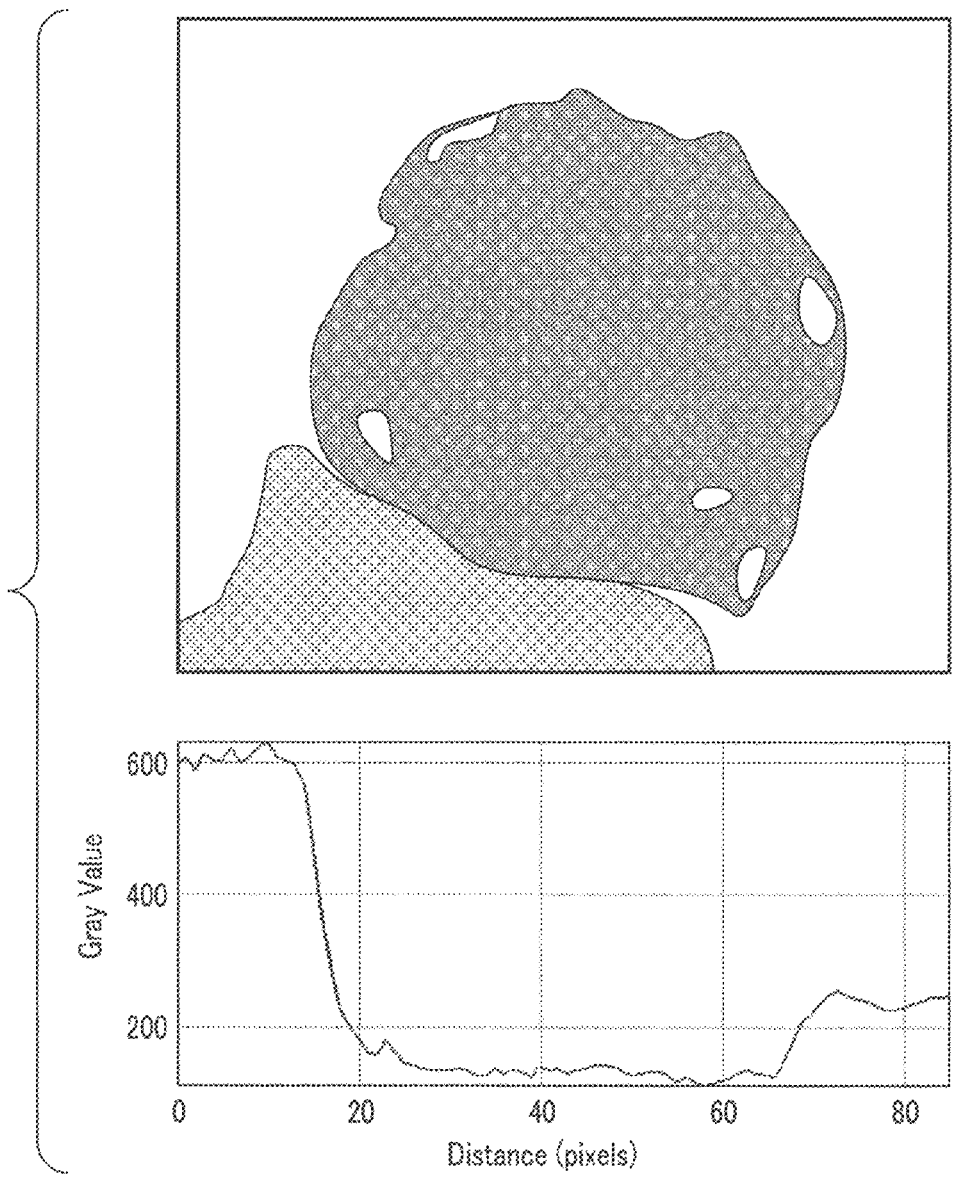
FIG. 9C shows an example of the blended frame.

As shown in FIG. 8, a ROI 804 is defined from ROI of the mask frame 806 and placed in the re-projected contrast frame 802. The re-projected contrast frame is calculated from re-projection of contrast image, and thus, theoretically matches with the corresponding contrast frame 810. The ROI of the re-projected contrast frame 804 is blended with the ROI of the mask frame 806 and generates a blended ROI 808. The blended ROI 808 is used to register the contrast frames 810 by calculating cross-correlation of blended ROI 808 with the displaced ROI in contrast frame 810. FIG. 9A is an example of the mask frame. FIG. 9B is an example of the contrast frame. FIG. 9C is an example of the blended mask frame. Compared to the mask frame, the blended mask frame matches better with the contrast frame resulting in a better apples-to-apples comparison and achieving more accurate registration.

In step 612, the processing circuitry registers the mask frames with the blended contrast frames, frame-pair-by-frame-pair, by performing a cross-correlation analysis of the ROIs between the blended frames and the contrast frames, with the search region depending on the maximum motion expected.

Figure 11:
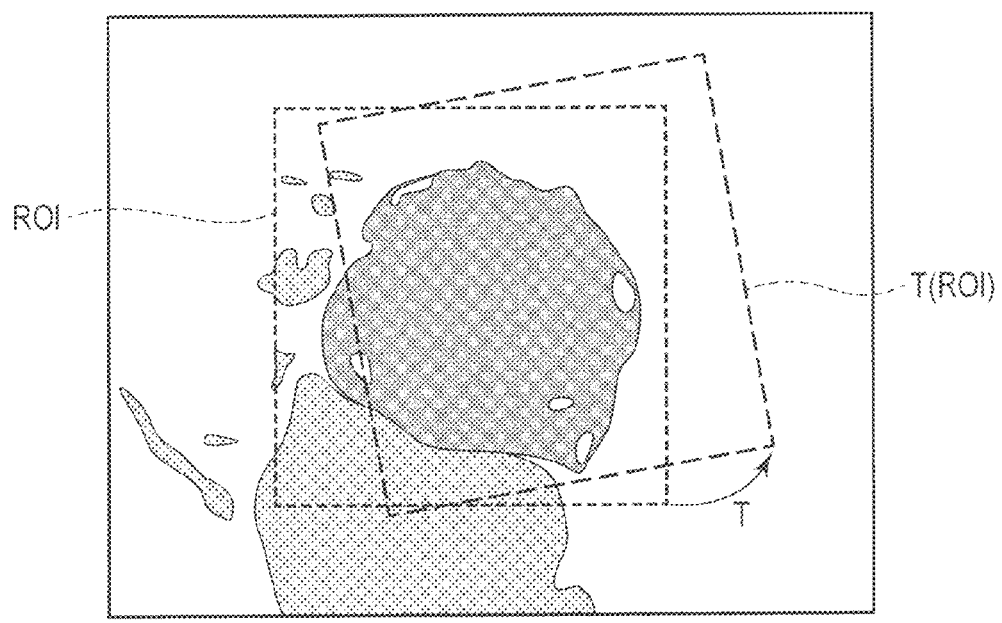
FIG. 11 shows an example of a transformation of the region-of-interest of the contrast frame.

In one embodiment, 2D translations are sufficient for the search. In another embodiment, registration includes both translation and rotation transformations in searching for the transformation T, as shown in FIG. 11, corresponding to the maximum value of the cross-correlation (e.g., the transformation that is the argument maximizing the overlap function between the blended mask frame and the transformed contrast frame).

Registration is the determination of a geometrical transformation that aligns points in one view of an object with corresponding points in another view of the object. From an operational perspective, the inputs of the registration process are two views. The output of the registration process is a geometrical transformation, which is a mathematical mapping from points in one view to points in a second view. To the extent that corresponding points are mapped to overlap each other and the overlap integral is maximized, the registration is successful.

When the mask frames are obtained, patients are instructed to remain static. However, injecting patients with contrast agent prior and during the acquisition of contrast frames causes discomfort to the patients, resulting in the patient's movement in response. Thus, the contrast frames are not usually aligned with mask frames because of the patient movement. FIG. 3C shows a misalignment of coil projections between the mask frame and the contrast frame. Therefore, registration between mask and contrast frames is required to align the mask frames and the contrast frames.

Figure 10A:
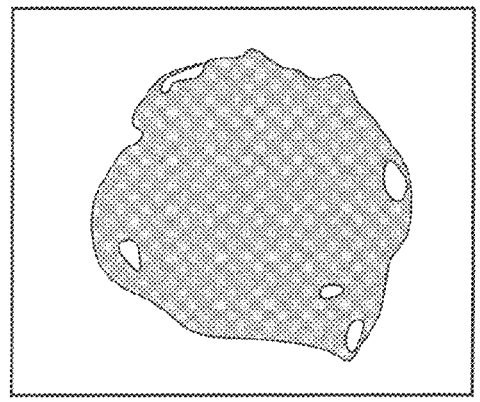
FIG. 10A shows an example of a region-of-interest of the mask frame.
Figure 10B:
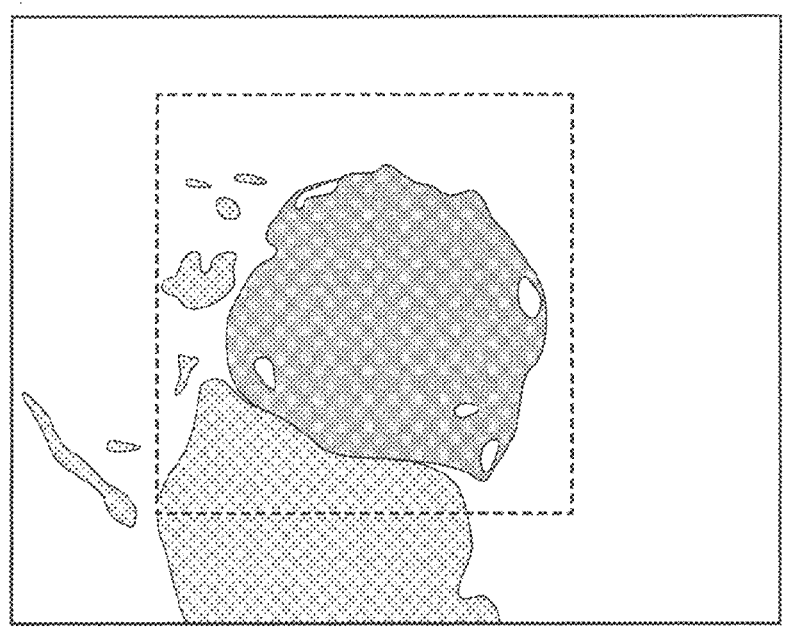
FIG. 10B shows an example of the region-of-interest of the contrast frame.

FIG. 10A illustrates an example of the ROI of the mask frame. The ROI of the mask frame is a pre-defined searching region in the mask frame. FIG. 10B illustrates an example of the ROI of the contrast frame. The ROI of the mask frame is the same size as the ROI of the contrast frame and has the same grid position of the flat panel detector as the ROI of the contrast frame. But, the patient's movement between the mask and contrast frames results in differences between the position of the metal between the two frames within their respective ROIs. Therefore, the cross-correlation needs to be performed to find the maximum value of the cross-correlation and to align the mask frame with the contrast frame.

Registration is performed by finding the maximum value of the cross-correlation function between the (blended) mask frame and the contrast frame, wherein the cross-correlation function can include both translations and rotations. Alternatively, registration can be performed by solving for the argument (i.e., transformation) that maximizes an overlap integral between the (blended) mask frame and the contrast frame, wherein the argument of the transformation operator includes both translations and rotations.

Next, a method of the registration of a (blended) mask frame $P_M(u, v)$ and the corresponding contrast frame $P_C(u, v)$ is described. Without loss of generality, only a single frame pair is described, but the same process can be used for each frame pair. The boundary-boxed ROI for mask frame can be described with reference to the top-left pixel $P_M(u_0, v_0)$ and the right-bottom pixel $P_M(u_1, v_1)$. Thus, the (blended) mask frame in ROI ("ROI of mask frame") can be expressed as $$P_{M,roi}(u', v') = P_M(u_0+u', v_0+v'), 0 \leq u' \leq u_1-u_0, 0 \leq v' \leq v_1-v_0. \quad (1)$$

Similarly, the corresponding contrast frame in ROI ("ROI of contrast frame")) can be expressed as $$P_{C,roi}(u', v') = P_C(u_0+u', v_0+v'), 0 \leq u' \leq u_1-u_0, 0 \leq v' \leq v_1-v_0. \quad (2)$$

The ROI of the contrast frame can be transformed by the transformation operator T, as shown in FIG. 11, and the attenuation values within the ROI of the transformed contrast frame can be re-sliced and interpolated onto a grid matching the (blended) mask frame for easy calculation of the overlap integral. A rigid transformation (defined as rotation and translation) of the ROI in the contrast frame can be defined as $$(u_{0,T}, v_{0,T}) \equiv T(u_0, v_0) = R_\theta(u_0, v_0) + (\Delta u, \Delta v) \text{ and}$$

$$(u_{1,T}, v_{1,T}) \equiv T(u_1, v_1) = R_\theta(u_1, v_1) + (\Delta u, \Delta v); \text{ and} \quad (3)$$

the contrast frame in transformed ROI is $$P_{C,roi}(u', v', T) = P_C((u_{0,T}, v_{0,T}) + u'\vec{u} + v'\vec{v}), 0 \leq u' \leq u_1-u_0, 0 \leq v' \leq v_1-v_0, \quad (4)$$

wherein $\vec{u}$ and $\vec{v}$ are normalized vectors along transformed u and v directions. The transformation of ROI image in contrast frame can be implemented by re-slicing and image interpolation to obtain an image grid with a matching size $(u_1-u_0, v_1-v_0)$ with the ROI of the (blended) mask frame. In one implementation, the cross-correlation between ROI of mask and transformed ROI of contrast frames can be expressed by $$CC(T) = \frac{1}{(u_1-u_0)(v_1-v_0)} \times \quad (5)$$

$$\sum_{u'=0}^{u_1-u_0}\sum_{v'=0}^{v_1-v_0}(P_{M,roi}(u',v')-\overline{P}_{M,roi})(P_{C,roi}(u',v',T)-\overline{P}_{C,roi}),$$

wherein $\overline{P}_{M,roi}$ and $\overline{P}_{C,roi}$ are the average in ROI of mask frame $P_{M,roi}(u', v')$ and the average in ROI of transformed contrast frame $P_{C,roi}(u', v', T)$, respectively. Registration occurs by finding the transformation that maximizes the above cross-correlation. For example, an optimal transformation maximizing the cross-correlation between ROIs of mask and contrast can be obtained using a brute force search within a pre-defined searching region so that a transformation argument is obtained that maximizes the cross-correlation as expressed by $$\tilde{T}=\arg\max_T CC(T). \quad (6)$$

The registered contrast frame then becomes $$P_{C,reg}(u,v)=P_C(\tilde{T}(u,v)). \quad (7)$$

The registered contrast frame can be obtained by image re-slicing and interpolation of the transformed frame. In one implementation, a stochastic search method, such as a genetic algorithm, can be used rather than the brute force search. In one implementation, a gradient search method can be used rather than the brute force search. Any known search method can be used to optimize the transformation argument of the cross-correlation function.

In step 614, the processing circuitry separates the registered mask frames from the contrast mask frames, frame-pair-by-frame-pair. A noise-cleaning filter is used for removing the residual pixels representing metal that is not eliminated in step 612.

In step 616, the processing circuitry performs reconstruction and obtains a metal-artifact-free image volume.

In one embodiment, a judgment function can be used to assist in subtracting the metal artifacts. The judgment function is performed in an ROI for a mask frame and in the same ROI for a contrast frame. Next, the two frames are compared in order to determine whether the transformation reconciling the two extracted frames are dominated by a translation or a rotation. If the rotation is smaller than a certain threshold value, then the transformation is presumed to be dominated by a translation transformation.

Additionally, a judgment function can be used for the completely different purpose of deciding whether or not a patient has moved enough to merit registration. If the patient has not moved enough to merit registration, then the registration step and all accompanying prerequisite steps can be omitted, resulting in significant savings in computational burden.

In one implementation, two types of judgment functions are used: an image-wise judgment function and a frame-wise judgment function. In the image-wise judgment function all of the frames for the entire image are evaluated and a determination is made regarding whether all of the contrast frames for the image require registration. In the frame-wise judgment function, each frame pair (i.e., contrast frame and corresponding mask frame) is evaluated separately to determine whether registration is required for that particular frame pair.

In one implementation, the judgment function can be realized by calculating the entropy of a difference frame between mask and contrast images within a ROI without registration. If the calculated entropy falls outside a predetermined range, then the image-wise judgment function determines that registration is required.

In one implementation, the judgment function can be realized by calculating the number of values less than a predetermined value for a difference frame, which is the difference between mask and contrast frames within a ROI without registration. For example, the contrast agent increases absorption so that the contrast frame minus the mask frame should yield only positive values or values close to zero. Because substantially negative values in the difference frame are indicative of a displacement of the contrast frame relative to the mask frame, the number of negative pixels in the difference frame less than a predetermined threshold (e.g., substantial less than zero) would be indicative of the magnitude of the displacement. Thus, the judgment function would determine when the number of pixels satisfying this first criteria (i.e., having pixel values below the first threshold for being substantially negative) exceeds a number-of-pixels threshold, then the contrast frame requires registration.

Referring now to FIG. 12, a flowchart 1200 is shown describing a method performed by processing circuitry for removing the indications of metal artifacts from 3D-DSA CT reconstructed acquisitions with the above-described judgment functions.

In step 1202, the processing circuitry generates a mask volume image by performing a first reconstruction using mask frames. This step is similar to step 602.

In step 1204, the processing circuitry identifies metal voxels by thresholding out all voxel values above a predetermined user threshold from the mask image. This step is similar to step 604.

In step 1206, the processing circuitry defines a region-of-interest (ROI) that contains metal in both the mask frames and the contrast frames. This step is similar to step 606.

Figure 12A:
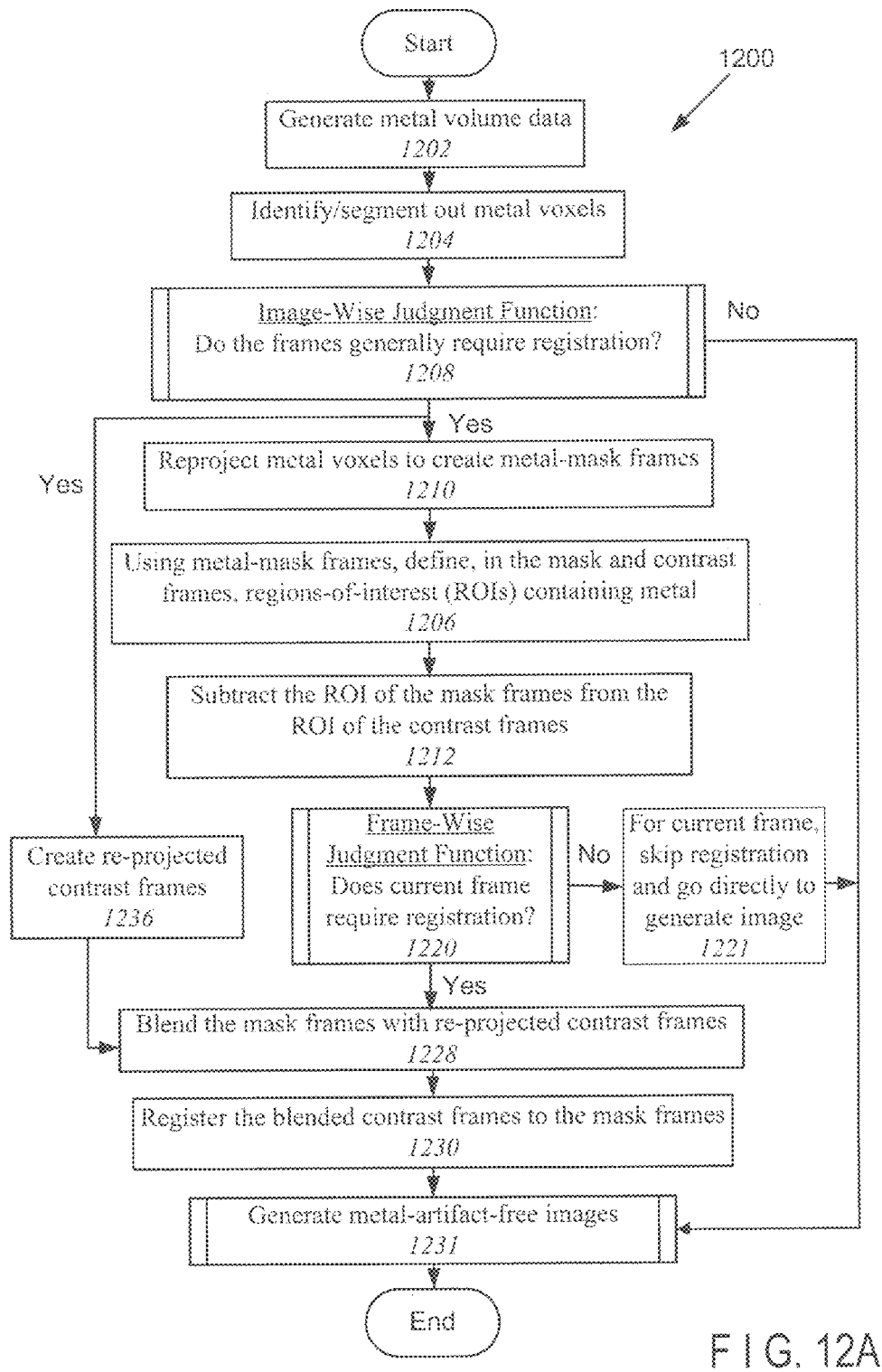
FIG. 12A shows a flow chart of one implementation of a method using judgment functions to reconstruct a contrast image representing the difference between a mask frame and a contrast frame, wherein the final contrast image is free of metal artifacts.
Figure 12B:
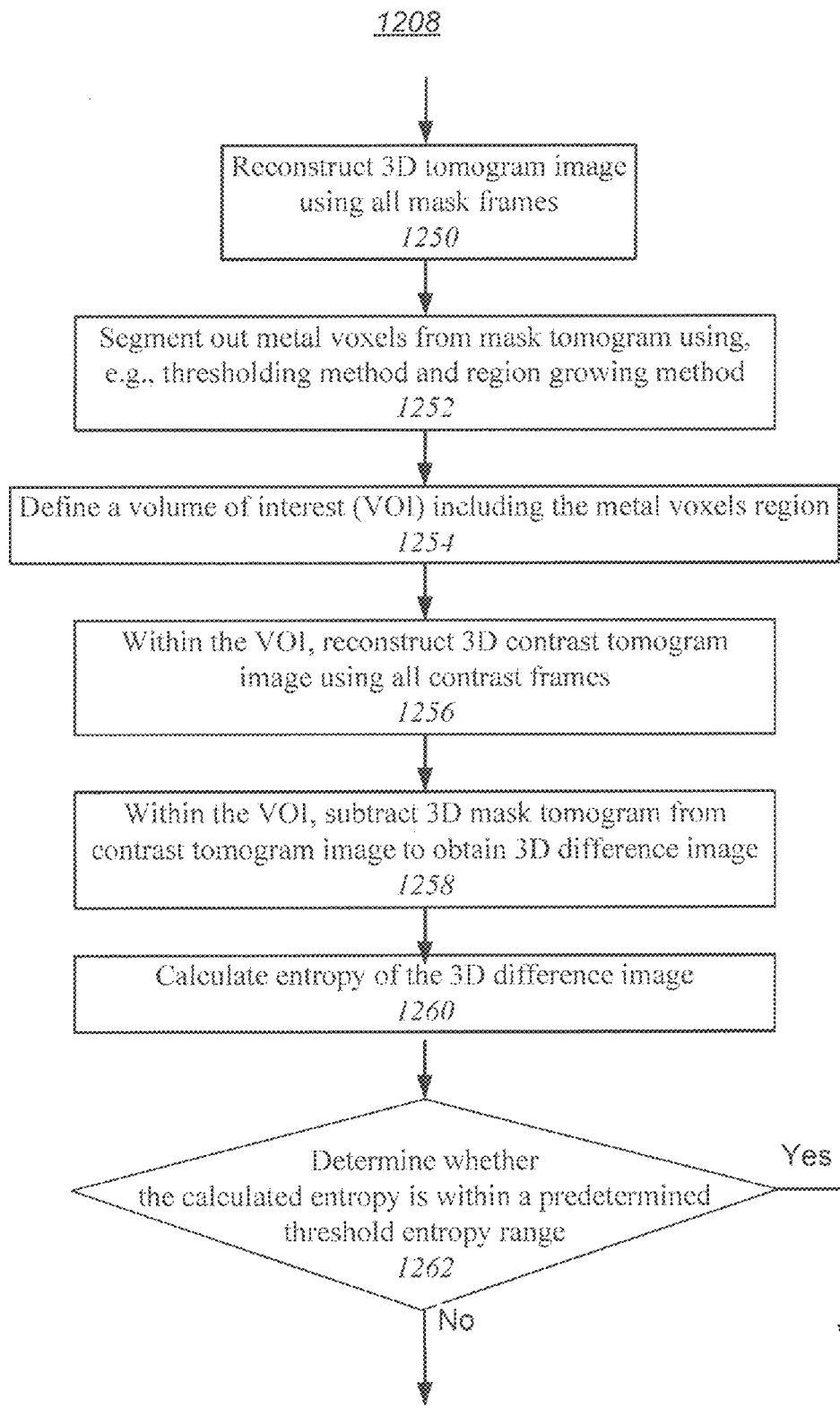
FIG. 12B shows a flow chart of one implementation of a process using image-wise judgment functions to determine the desirability of frame registration between contrast frames and mask frames.

In process 1208, the processing circuitry determines whether to register the contrast frames to the corresponding mask frames based on an image-wise judgment function, as shown in FIG. 12B. As part of process 1208, the processing circuitry calculates the entropy within a volume of interest (VOI) for the difference image between a reconstructed image of the mask frames and a reconstructed image of the contrast frames.

In step 1250 of process 1208, the mask frames are used to reconstruct a three-dimensional tomographic image (i.e., a tomogram).

In step 1252 of process 1208, the voxels corresponding to the metal regions are segmented out and flagged using a thresholding method and a region growing method.

In step 1254 of process 1208, a VOI is defined to include the metals voxels.

In step 1256 of process 1208, a three-dimensional tomographic image is reconstructed from the contrast frames. This reconstructed image from the contrast frames includes at least the VOI.

In step 1258 of process 1208, a difference image is calculated within the VOI by subtracting contrast image within the VOI from the mask image within the VOI. In step 1260 of process 1208, the entropy of the difference image is calculated. The randomness of voxels is measured by the entropy of the image. For voxels with large variations among the voxels, the entropy will be approximately one half. For the voxels having only small variation, the entropy will either be close to zero or close to one. When the patient moves around and the coil images cannot be subtracted out, streaks might be left in the subtracted frame, resulting in large variations in the difference frame. In this case, the entropy can be a value close to one half.

In step 1262 of process 1208, the processing circuitry determines whether the obtained entropy is within a predetermined threshold entropy range. If the calculated entropy is within the predetermined threshold entropy range, the processing circuitry proceeds to process 1220 and also to step 1236. If the calculated entropy is outside of the predetermined threshold entropy, the processing circuitry aborts registration for all contrast frames.

The predetermined threshold entropy p can be determined from statistical criterion by using a pool of 3D-DSA patient datasets to search for the best value. And p is usually very close to 0. When $0.5-p \leq E \leq 0.5+p$, $0 < p \leq 0.5$ and E is the obtained entropy, the subtraction is very random and the processing circuitry performs the registration.

In step 1210, the processing circuitry performs a re-projection of the metal voxels of the metal volume image to create the mask frames.

In step 1212, the processing circuitry subtracts the mask frames from the contrast frames within the ROI, frame-pair-by-frame-pair.

Figure 12C:
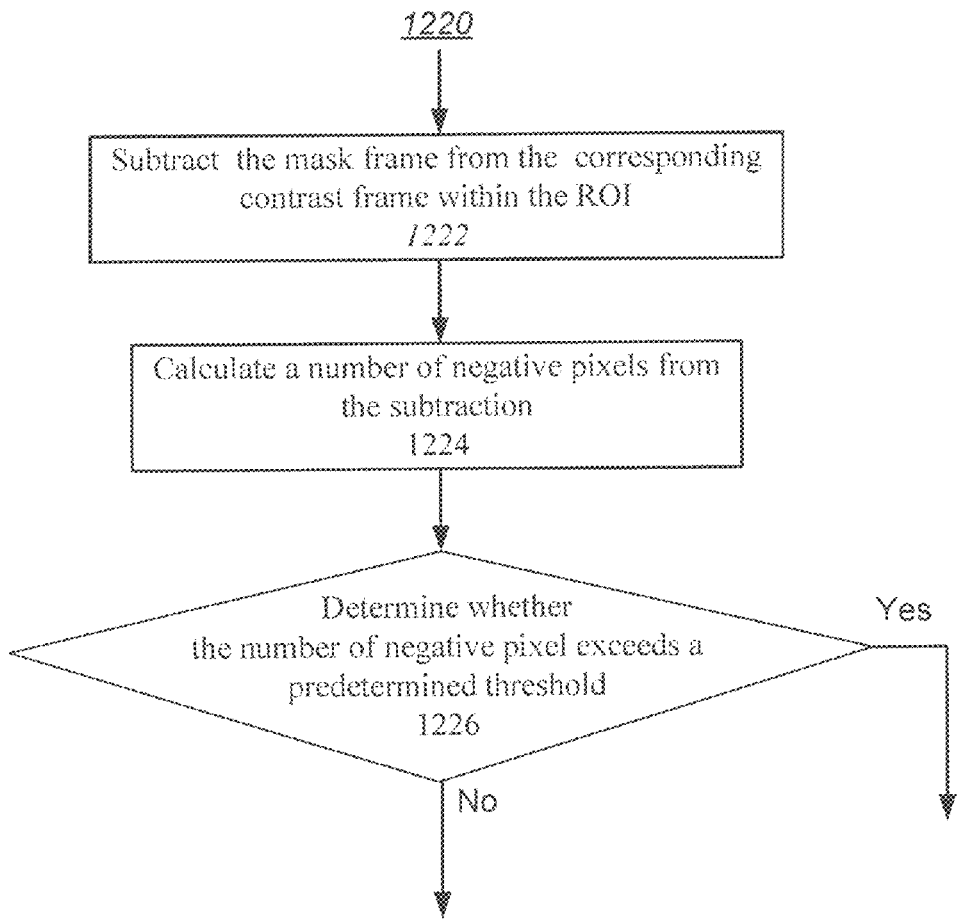
FIG. 12C shows a flow chart of one implementation of a process using frame-wise judgment functions to determine the desirability of frame registration between a contrast frame and a mask frame.
Figure 12D:
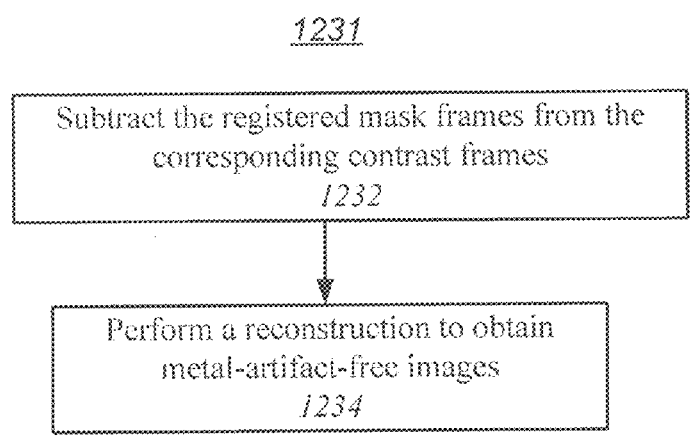
FIG. 12D shows a flow diagram of one implementation of a process to reconstruct a difference image corresponding to a difference between a mask and a contrast frame.

In process 1220, the processing circuitry determines whether to register the contrast frames to the corresponding mask frames based on a frame-wise judgment function, as shown in FIG. 12C.

In step 1222 of process 1220, the processing circuitry subtracts the mask frame from the corresponding contrast frame within the ROI, similar to step 1212.

In step 1224 of process 1220, the processing circuitry calculates a number of negative pixels in the subtraction frame obtained in step 1222.

Because the contrast frames include attenuation due to the contrast agent in addition to all of the attenuating objects in the mask frames, subtracting the mask frame from the contrast frame general results in a positive attenuation (e.g., regions with contrast agent) or zero attenuation (e.g., in regions without contrast agent). However, when the contrast and mask frames are imperfectly aligned, then a strongly absorbing region of the mask frame may overlap a weakly absorbing regions of the contrast frame, resulting in a difference between the two attenuations that is negative— especially where the strongly absorbing region of the mask frame corresponds to a metal stent or coil and the weakly absorbing region in the contrast frame is soft matter and/or contrast agent. Thus, when the metal projection of the coil/stent is not aligned between the mask frame and the contrast frame, the difference frame is likely to include a region of large negative values, and the area of this region (i.e., the number of pixels having large negative values) relative to the area of metal absorption in the mask frame is an indicator of magnitude of the offset between the mask and contrast frames.

In step 1226 of process 1220, the processing circuitry determines whether the calculated number of negative pixels exceeds a predetermined threshold of negative pixels. If the number of the negative pixels is larger than the predetermined threshold of negative pixels, the processing circuitry performs step 1228 followed by step 1230 with respect to the mask frame and the contrast frame corresponding to the difference evaluated in step 1226.

Otherwise, for the given frame under consideration, the processing circuitry skips the registration process by skipping the steps 1228 and 1230 and proceeding directly to step 1231 through step 1221 for the given mask frame and contrast frame pair under consideration. If the number of negative pixels falls below the predetermined threshold, then for that given frame, it is determined that the alignment of that particular mask frame and contrast frame pair is sufficient that registration can be skipped for that pair. In process 1220, the sufficiency of the alignment between a pair of mask and contrast frames is determined on a frame-wise basis, with each mask frame and contrast frame pair being considered independently, and some pairs possibly being directed to step 1221 to skip the registration process, while other pairs are possibly directed to step 1228 to begin the registration process. Each mask frame and contrast frame pair will be directed to either step 1221 or step 1228.

Figure 13A:
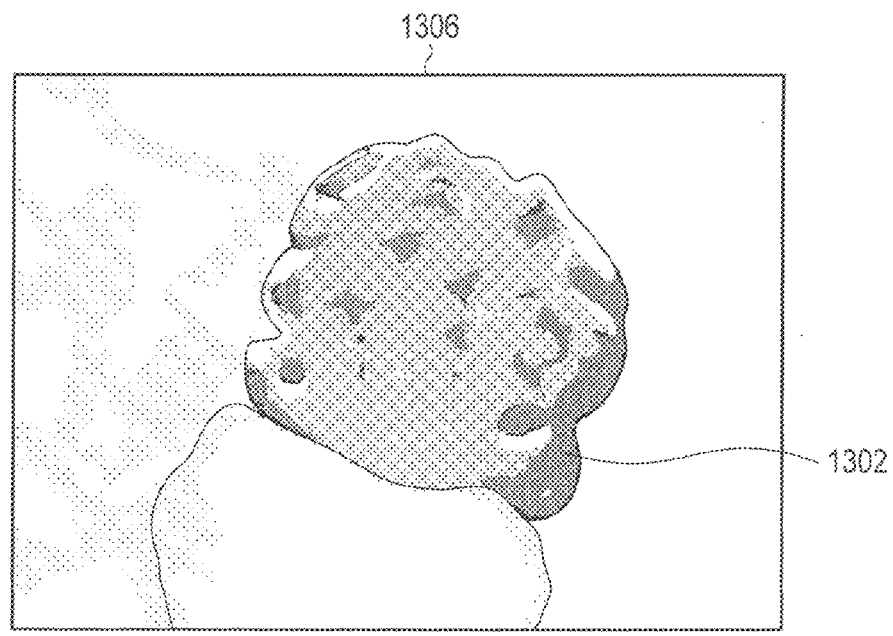
FIG. 13A shows a difference frame of a mask frame and a contrast frame, wherein a first offset between the mask frame and the contrast frame results in negative pixel values on the bottom-right side of the metal image.
Figure 13B:
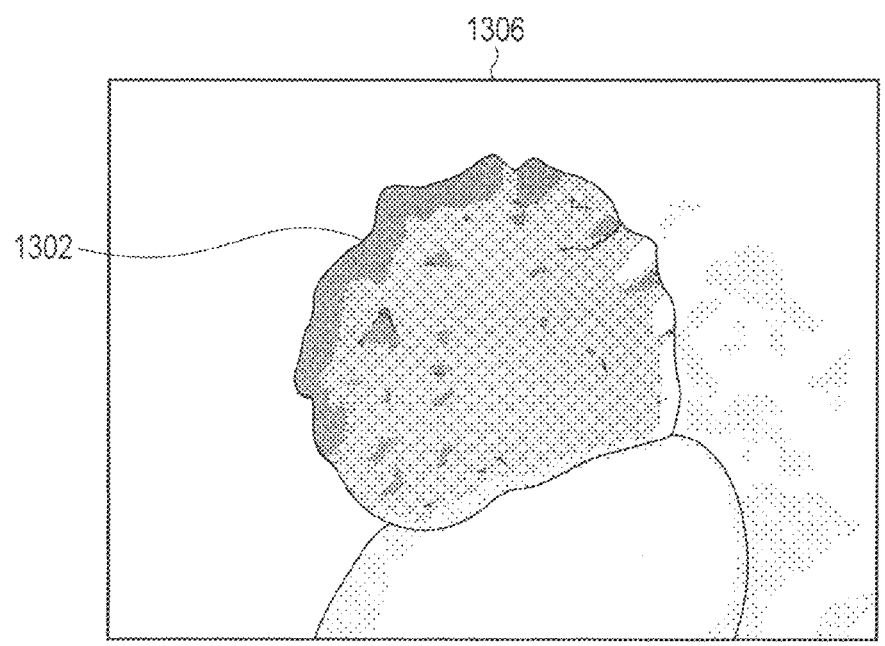
FIG. 13B shows a difference frame of a mask frame and a contrast frame, wherein a second offset between the mask frame and the contrast frame results in negative pixel values on the top-left side of the metal image.

FIGS. 13A and 13B illustrate a difference frame 1302 for which negative pixels result due to misalignment between the mask frame and the contrast frame. When the coil pixel is misaligned between the mask frame and the contrast frame, the negative subtraction appears. In one implementation, a sum of the negative pixel values of the difference frame can be used for the judgment function. However, calculating the sum of the negative pixel values of the difference frame can be difficult. Thus, in an alternative implementation, a ratio of the area of negative subtraction to the area of the coil projection can be used for the judgment function. This ratio r is defined as:

$$r = \text{(a number of negative pixels/a number of coil pixels)}.$$

If $r \leq 5\%$, the processing circuitry passes the judgment function and performs the registration in step 1228. If $r \leq 5\%$, the processing circuitry aborts the registration for this mask frame and contrast frame. The optimum r can also be pre-determined from a pool of patient datasets.

In step 1236, the processing circuitry generates re-projected contrast frames. The method is described in process 617.

In step 1228, the processing circuitry blends the mask frames with the re-projected contrast frames to generate blended contrast frames. This step is similar to step 610.

In step 1230, the processing circuitry registers the mask frames with the blended contrast frames, frame-pair-by-frame-pair, by performing a cross-correlation analysis of the ROIs between the blended frames and the contrast frames, with the search region depending on the maximum motion expected. This step is similar to step 612.

In process 1231, difference frames are calculated and a metal-artifact-free contrast image is reconstructed from the difference frames. This process is similar to process 615.

In step 1232 of process 1231, the processing circuitry separates the registered mask frames from the contrast mask frames, frame-pair-by-frame-pair. This step is similar to step 614.

In step 1234 of process 1231, the processing circuitry performs reconstruction and obtains a metal-artifact-free image volume. This step is similar to step 616.

Figure 14:
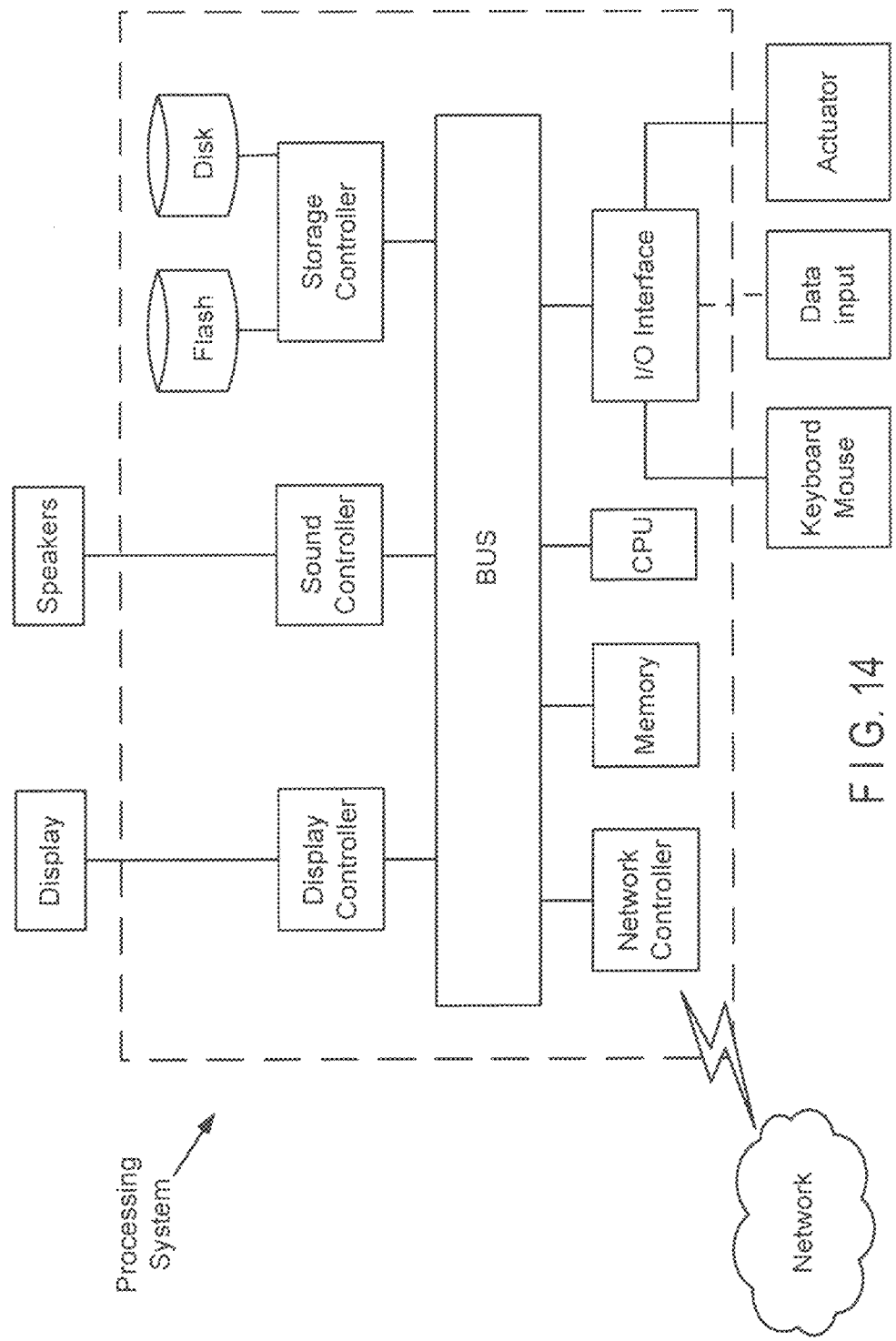
FIG. 14 shows a schematic diagram of one implementation of a processing system.
Figure 15:
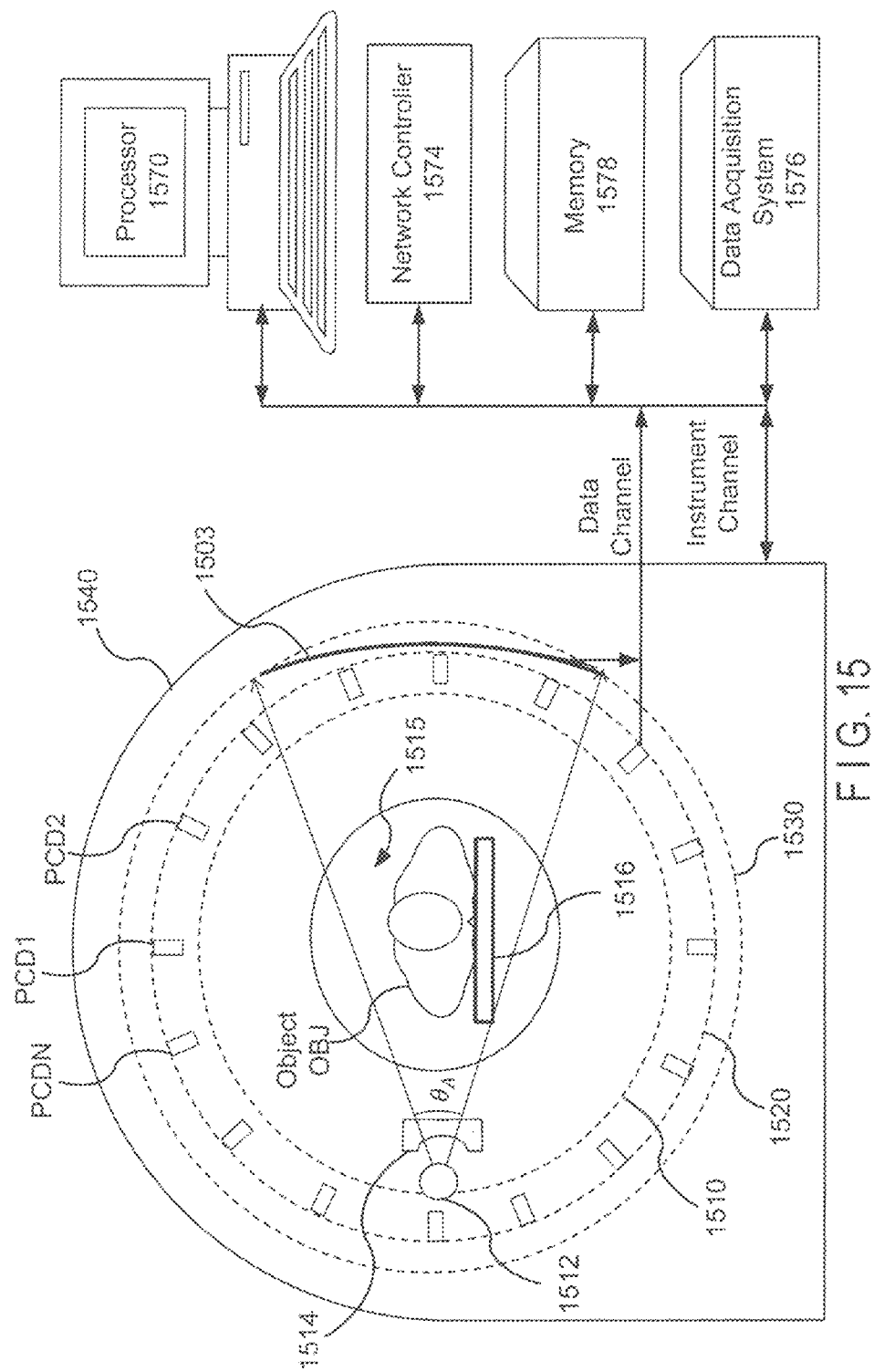
FIG. 15 shows a schematic diagram of one implementation of a CT-scanner using a hybrid configuration having both energy-integrating detectors and energy-resolving detectors.

An example of a processing system is illustrated in FIG. 14, which is an example of a implementation of the processing circuitry 160 of FIG. 1 and the processor 1570 of FIG. 15. The processing circuitry 6 can be a hardware device, e.g., a CPU that has been specifically configured to execute one or more computer programs that cause the CPU to perform the functions illustrated in the flowchart of FIGS. 6 and 12. In particular, this illustrative processing system can be implemented using one or more microprocessors or the equivalent, such as a central processing unit (CPU) and/or at least one application-specific processor ASP (not shown). A microprocessor is a circuit or circuitry that utilizes a computer readable storage medium, such as a memory circuit (e.g., ROM, EPROM, EEPROM, flash memory, static memory, DRAM, SDRAM, and their equivalents), configured to control the microprocessor to perform and/or control the processes and systems of this disclosure, and configured to execute the algorithms described herein. Other storage mediums can be controlled via a controller, such as a disk controller, which can controls a hard disk drive or optical disk drive.

The microprocessor or aspects thereof, in alternate implementations, can include or exclusively include a logic device for augmenting or fully implementing aspects of this disclosure. Such a logic device includes, but is not limited to, an application-specific integrated circuit (ASIC), a field programmable gate array (FPGA), a generic-array of logic (GAL), and their equivalents. The microprocessor can be a separate device or a single processing mechanism. Further, this disclosure can benefit from parallel processing capabilities of a multi-cored CPU and a graphics processing unit (GPU) to achieve improved computational efficiency. One or more processors in a multi-processing arrangement may also be employed to execute sequences of instructions contained in memory. Alternatively, hard-wired circuitry may be used in place of or in combination with software instructions. Thus, the illustrative implementations discussed herein are not limited to any specific combination of hardware circuitry and software.

In another aspect, results of processing in accordance with this disclosure can be displayed via a display controller to a monitor. The display controller preferably includes at least one graphic processing unit, which can be provided by a plurality of graphics processing cores, for improved computational efficiency. Additionally, an I/O (input/output) interface is provided for inputting signals and/or data from microphones, speakers, cameras, a mouse, a keyboard, a touch-based display or pad interface, etc., which can be connected to the I/O interface as a peripheral. For example, a keyboard or a pointing device for controlling parameters of the various processes or algorithms of this disclosure can be connected to the I/O interface to provide additional functionality and configuration options, or control display characteristics. Moreover, the monitor can be provided with a touch-sensitive interface for providing a command/instruction interface.

The above-noted components can be coupled to a network, such as the Internet or a local intranet, via a network interface for the transmission or reception of data, including controllable parameters. A central bus is provided to connect the above hardware components together and provides at least one path for digital communication there between.

The data acquisition system 150, the processing circuitry 160, and the memory 170 of FIG. 1 can be implemented utilizing one or more processing systems in accordance with the illustrative implementation shown in FIG. 14. Also, the processor 1570, network controller 1574, memory 1578, and data acquisition system 1576 of FIG. 15 can be implemented utilizing one or more processing systems in accordance with the illustrative implementation shown in FIG. 14. In particular, one or more circuits or computer hardware units coinciding with one or more of the devices illustrated in FIG. 1 can provide for the functions of the data acquisition system 150, the processing circuitry 160, and the memory 170 (collectively or separately). Also, one or more circuits or computer hardware units coinciding with one or more of the devices illustrated in FIG. 15 can provide for the functions of the processor 1570, network controller 1574, memory 1578, and data acquisition system 1576 of FIG. 15 (collectively or separately). The functional processing described herein can also be implemented in specialized circuitry or one or more specialized circuits including circuits to perform the described processing. Such circuits can be a part of a computer processing system or a discrete device that is interconnected to other systems. A processing circuitry in accordance with this disclosure can also be programmed to or configured to execute the functional processing described herein by computer code elements.

Further, the processing systems, in one implementation, can be connected to each other by a network or other data communication connection. One or more of the processing systems can be connected to corresponding actuators to actuate and control movement of the gantry, the X-ray source, and/or the patient bed.

Suitable software can be tangibly stored on a computer readable medium of a processing system, including the memory and storage devices. Other examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read. The software may include, but is not limited to, device drivers, operating systems, development tools, applications software, and/or a graphical user interface.

Computer code elements on the above-noted medium may be any interpretable or executable code mechanism, including but not limited to scripts, interpretable programs, dynamic link libraries (DLLs), Java classes and complete executable programs. Moreover, parts of the processing of aspects of this disclosure may be distributed for better performance, reliability and/or cost.

The data input portion of the processing system accepts input signals from a detector or an array of detectors by, e.g., respective wired connections. A plurality of ASICs or other data processing components can be provided as forming the Data Input portion, or as providing input(s) to the data input portion. The ASICs can receive signals from, respectively, discrete detector arrays or segments (discrete portions) thereof. When an output signal from a detector is an analog signal, a filter circuit can be provided, together with an analog-to-digital converter for data recording and processing uses. Filtering can also be provided by digital filtering, without a discrete filter circuit for an analog signal. Alternatively, when the detector outputs a digital signal, digital filtering and/or data processing can be performed directly from the output of the detector.

In one implementation, the method of registering and subtracting mask and contrast frames to reconstruct DSA images can be performed using a CT apparatus having either energy-integrating detectors, or X-ray energy-resolving detectors (e.g., photon-counting detectors), and a hybrid system having a combination of energy-integrating detectors and energy-resolving detectors. FIG. 15 shows a schematic view of an example of a hybrid CT scanner system having energy-integrating detectors arranged in a third-generation geometry and photon-counting detectors (PCDs) arranged in a fourth-generation geometry. The CT scanner is arranged in a coupled ring topology with the X-ray source 1512 inside the ring of PCDs and the X-ray detector unit 1503 is outside the ring of PCDs, as discussed in U.S. patent application Ser. No. 13/426,903, incorporated herein by reference in its entirety. A CT scanner having only energy-integrating detectors can be obtained by removing the PCDs in FIG. 15. A CT scanner having only energy-resolving detectors can be obtained by removing the X-ray detector unit 1503 in FIG. 15.

Illustrated in FIG. 15 is an implementation for placing the PCDs in a predetermined fourth-generation geometry in combination with a detector unit 1503 in a predetermined third-generation geometry in a CT scanner system. The diagram illustrates relative positions among an object OBJ to be scanned resting on a table 1516, an X-ray source 1512, a collimator/filter 1514, an X-ray detector 1503, and photon-counting detectors PCD 1 through PCDN. The PCDs have a front surface, oriented towards the object OBJ and a back surface oriented away from the object OBJ. X-rays traveling through the object OBJ are either detected by the PCDs (at the front surface) or pass through the spaces between the sparsely arranged PCDs and are detected by the tightly packed energy-integrating detectors in the X-ray detector 1503.

Also shown in FIG. 15 is circuitry and hardware for acquiring, storing, processing, and distributing X-ray projection data. The circuitry and hardware include: a processor 1570, a network controller 1574, a memory 1578, and a data acquisition system 1576.

In one implementation, the X-ray source 1512 and the collimator/filter 1514 are fixedly connected to a rotational component 1510 that is rotatably connected to a gantry 1540. The X-ray detector 1503 is similarly fixedly connected to a rotational component 1530 that is rotatably connected to the gantry 1540. While, the PCDs are fixedly connected to a circular component 1520 that is fixedly connected to the gantry 1540. The gantry 1540 houses many pieces of the CT scanner.

The gantry of the CT scanner also includes an open aperture 1515 enabling the object OBJ that is arranged on a table 1516 positioned in a projection plane of the X-rays traveling from the X-ray source to the PCDs and detector unit 1503. The "projection plane" is a volume wherein X-rays pass from the X-ray source 1512 to the detectors including the PCDs and the detector unit 1503. The "object space" is the intersection of the projection plane and the open aperture 1515 of the gantry. The "image space" includes the union of projection planes corresponding to all projection angles of the X-ray source 1512 as the X-ray source 1512 rotates around the aperture of the gantry.

A scan is performed when an object OBJ occupies the object space and the X-ray source is rotated through a series of projection angles with the CT scanner acquiring projection data of the X-ray transmission/attenuation through the object OBJ at each projection angle.

In general, the photon-counting detectors PCD1 through PCDN each output a photon count for each of a predetermined number of energy bins. In addition to the photon-counting detectors PCD1 through PCDN arranged in the fourth-generation geometry, the implementation shown in FIG. 15 includes a detector unit 1503 having energy-integrating detectors arranged in a conventional third-generation geometry. The detector elements in the detector unit 1503 can be more densely placed along the detector unit surface than the photon-counting detectors.

In one implementation, the photon-counting detectors are sparsely placed around the object OBJ in a predetermined geometry such as a circle. For example, the photon-counting detectors PCD1 through PCDN are fixedly placed on a predetermined second circular component 1520 in a gantry. In one implementation, the photon-counting detectors PCD1 through PCDN are fixedly placed on the circular component 1520 at predetermined equidistant positions. In an alternative implementation, the photon-counting detectors PCD1 through PCDN are fixedly placed on the circular component 1520 at predetermined non-equidistant positions. The circular component 1520 remains stationary with respect to the object OBJ and does not rotate during the data acquisition.

Both the X-ray source 1512, collimator 1514 (e.g., a bow tie filter), and the detector unit 1503 rotate around the object OBJ while the photon-counting detectors PCD1 through PCDN are stationary with respect to the object OBJ. In one implementation, the X-ray source 1512 projects X-ray radiation with a predetermined source fan beam angle $\theta_A$ towards the object OBJ while the X-ray source 1512 rotates around the object OBJ outside the sparsely placed photon-counting detectors PCD1 through PCDN. Furthermore, the detector unit 1503 is mounted at a diametrically opposed position from the X-ray source 1512 across the object OBJ and rotates outside the stationary circular component 1520, on which the photon-counting detectors PCD1 through PCDN are fixed in a predetermined sparse arrangement.

In one implementation, the X-ray source 1512 optionally travels a helical path relative to the object OBJ, wherein the table 1516 moves the object OBJ linearly in a predetermined direction perpendicular to the rotational plane of the rotating portion 1510 as the rotating portion 1510 rotates the X-ray source 1512 and detector unit 1503 in the rotational plane.

The motion of the rotating portion 1510 around the object OBJ is controlled by a motion control system. The motion control system can be integrated with a data acquisition system or can be separate providing one way information regarding the angular position of the rotating portion 1510 and the linear position of the table 1516. The motion control system can include position encoders and feedback to control the position of the rotating portion 1510 and the table 1516. The motion control system can be an open loop system, a closed loop system, or a combination of an open loop system and a closed loop system. The motion control system can use linear and rotary encoders to provide feedback related to the position of the rotating portion 1510 and the position of the table 1516. The motion control system can use actuators to drive the motion of the rotating portion 1510 and the motion of the table 1516. These positioners and actuators can include: stepper motors, DC motors, worm drives, belt drives, and other actuators known in the art.

The CT scanner also includes a data channel that routes projection measurement results from the photon counting detectors and the detector unit 1503 to a data acquisition system 1576, a processor 1570, memory 1578, network controller 1574. The data acquisition system 1576 controls the acquisition, digitization, and routing of projection data from the detectors. The data acquisition system 1576 also includes radiography control circuitry to control the rotation of the annular rotating frames 1510 and 1530. In one implementation data acquisition system 1576 will also control the movement of the bed 1516, the operation of the X-ray source 1512, and the operation of the X-ray detectors 1503. The data acquisition system 1576 can be a centralized system or alternatively it can be a distributed system. In an implementation, the data acquisition system 1576 is integrated with the processor 1570. The processor 1570 performs functions including reconstructing images from the projection data, pre-reconstruction processing of the projection data, and post-reconstruction processing of the image data.

The pre-reconstruction processing of the projection data can include a calibration, correcting for detector nonlinearities, polar effects, noise balancing, and material decomposition.

Post-reconstruction processing can include filtering and smoothing the image, volume rendering processing, and image difference processing as needed. The image reconstruction process can be performed using filtered back projection, iterative image reconstruction methods, or stochastic image reconstruction methods. Both the processor 1570 and the data acquisition system 1576 can make use of the memory 1576 to store, e.g., projection data, reconstructed images, calibration data and parameters, and computer programs.

The processor 1570 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 1578 can be a hard disk drive, CD-ROM drive, DVD drive, FLASH drive, RAM, ROM or any other electronic storage known in the art.

The network controller 1574, such as an Intel Ethernet PRO network interface card from Intel Corporation of America, can interface between the various parts of the CT scanner. Additionally, the network controller 1574 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In one implementation, the X-ray source 1512 is optionally a single energy source. In another implementation, the X-ray source 1512 is configured to perform a kV-switching function for emitting X-ray radiation at a predetermined high-level energy and at a predetermined low-level energy. In still another alternative embodiment, the X-ray source 1512 is a single source emitting a broad spectrum of X-ray energies. In still another embodiment, the X-ray source 1512 includes multiple X-ray emitters with each emitter being spatially and spectrally distinct.

The detector unit 1503 can use energy-integrating detectors such as scintillation or phosphor elements with photomultiplier tubes or avalanche photo-diodes to detect the resultant photons from an X-ray detection event resulting from the X-ray radiation interacting with the scintillator/phosphor elements. The scintillator/phosphor elements can be crystalline (e.g., NaI(Tl), CsI(Tl), CsI(Na), CsI(pure), CsF, KI(Tl), LiI(Eu), $BaF_2$, $CaF_2(Eu)$, ZnS(Ag), $CaWO_4$, $CdWO_4$, YAG(Ce), $Y_3Al_5O_{12}(Ce)$, GSO, LSO, $LaCl_3(Ce)$, $LaBr_3(Ce)$, LYSO, BGO, $LaCl_3(Ce)$, $LaBr_3(Ce)$, $C_{14}H_{10}$, $C_{14}H_{12}$, and $C_{10}H_8$), an organic liquid (e.g., an organic solvent with a fluor such as p-terphenyl ($C_{18}H_{14}$), PBD ($C_{20}H_{14}N_2O$), butyl PBD ($C_{24}H_{22}N_2O$), or PPO ($C_{15}H_{11}NO$)), a plastic (e.g., a flour suspended in a solid polymer matrix), or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs). Semiconductor based direct X-ray detectors generally have much faster time response than indirect detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

Having obtained spectral CT projection data, the spectral CT imaging system using the processor 1570 will perform a material decomposition on the spectral CT projection data to obtain projection lengths $L_1$ and $L_2$ corresponding respectively to a first and second material (e.g., a high-Z material such as bone and a low-Z material such as water). Performing this material decomposition is complicated by nonlinearities of the PCDs' response, by characteristic X-ray escape, and by beam hardening due to variations of the absorption coefficient as a function of X-ray energy.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:

1. A radiation diagnosis apparatus to improve registration and reduce artifacts in digital subtraction computed tomography, the apparatus comprising:
processing circuitry configured to
identify first regions corresponding to a metal artifact based on a plurality of first frames at a plurality of angles or a plurality of second frames at the plurality of angles, the plurality of first frames including projection data from a CT scan performed at a first time, and the plurality of second frames including projection data from a CT scan performed at a second time, which is different from the first time,
correct misregistrations between the first frames and the second frames based on the first regions, generate subtraction frames between the first frames and the second frames after correcting the misregistrations, and reconstruct a first reconstructed image based on the subtraction frames respectively obtained at the plurality of angles.

2. The CT radiation diagnosis apparatus according to claim 1, wherein the the first region is a region that includes a metallic substance that forms an embolus in an aneurysm of a subject.

3. The radiation diagnosis apparatus according to claim 1, wherein the processing circuitry is further configured to identify the first region using a subtracted frame based on the first frame and the second frame.

4. The radiation diagnosis apparatus according to claim 1, wherein the processing circuitry is further configured to generate a second reconstructed image based on the plurality of first frames or the plurality of second frames, and to identify the first region in the second reconstructed image.

5. The radiation diagnosis apparatus according to claim 4, wherein a voxel matrix size of the second reconstructed image is smaller than that of the first reconstructed image.

6. The radiation diagnosis apparatus according to claim 1, wherein the processing circuitry is further configured to correct at least either the plurality of first frames or the plurality of second frames in such a manner that the first region in which an embolus is formed in an aneurysm of a subject in the plurality of frames and the first region in the plurality of second frames are registered.

7. The radiation diagnosis apparatus according to claim 4, wherein the processing circuitry is further configured to
reconstruct the first reconstructed image to have a first resolution and a first number of voxels; and
reconstruct the second reconstructed image to have a second resolution and a second number of voxels, wherein
the first number of voxels is less than the second number of voxels.

8. The radiation diagnosis apparatus according to claim 1, wherein the first frame is a mask frame, and the second frame is a contrast frame.

9. The radiation diagnosis apparatus according to claim 8, wherein the processing circuitry is further configured to
project the contrast frame at the plurality of projection angles to generate contrast re-projection frames;
blend each of the contrast frames with the corresponding contrast re-projection frame to generate respective blended mask frames;
register each of the contrast frames with the corresponding blended mask frame to align absorption features of the contrast frame with absorption features of the blended mask frame using a transformation that includes a translation.

10. The radiation diagnosis apparatus according to claim 9 wherein the transformation includes both the translation and a rotation.

11. The radiation diagnosis apparatus according to claim 9 wherein the processing circuitry is further configured to
register each blended mask frame with the corresponding contrast frame using a maximum value of a cross-correlation between the blended mask frame and the corresponding contrast frame to determine the transformation.

12. The radiation diagnosis apparatus according to claim 8, wherein the processing circuitry is further configured to define a plurality of second regions, each second region corresponding to a respective mask frame and a respective contrast frame and including a metal region, wherein registration of each contrast frame with the corresponding mask frame aligns absorption features of the contrast frame and the frame within the second region.

13. The radiation diagnosis apparatus according to claim 12, wherein the processing circuitry is further configured to
generate a plurality of third frames using the plurality of mask frames, wherein the plurality of third frames are metal-mask frames representing absorption of the object corresponding to metal, wherein the processing circuitry is configured to define the plurality of second regions using the metal regions of the plurality of third frames.

14. The radiation diagnosis apparatus according to claim 13, wherein the processing circuitry is further configured to generate the plurality of third frames by
reconstructing a mask image using the plurality of mask frames;
identifying metal voxels in the mask image; and
re-projecting the metal voxels at the plurality of projection angles to generate the plurality of third frames.

15. The radiation diagnosis apparatus according to claim 14, wherein the processing circuitry is further configured to identify metal voxels in the mask image using a threshold-and-region-growing method.

16. The radiation diagnosis apparatus according to claim 9, wherein the processing circuitry is further configured to
generate the contrast re-projection frames by using a threshold-and-region-growing method to segment the first reconstructed image, projecting the segmented first reconstructed image to generate a contrast re-projection mask for each projection angle of the plurality of projection angles, and then projecting the first contrast image at each projection angle using the corresponding contrast re-projection mask.

17. The radiation diagnosis apparatus according to claim 9, wherein the processing circuitry is further configured to blend each mask frame with the corresponding contrast re-projection frame by adding pixel-by-pixel, an absorption of the mask frame to an absorption of the corresponding contrast re-projection frame.

18. The radiation diagnosis apparatus according to claim 1, wherein the radiation diagnosis apparatus is an X-ray CT apparatus.

19. The radiation diagnosis apparatus according to claim 1, wherein the radiation diagnosis apparatus is a C-arm angio apparatus.

20. A radiation diagnosis method to improve registration and reduce artifacts in digital subtraction computed tomography, the method comprising:
identifying first regions corresponding to a metal artifact based on a plurality of first frames at a plurality of angles or a plurality of second frames at the plurality of angles, the plurality of first frames including projection data from a CT scan performed at a first time, and the plurality of second frames including projection data from a CT scan performed at a second time, which is different from the first time,
correcting misregistrations between the first frames and the second frames based on the first regions,
generating subtraction frames between the first frames and the second frames after correcting the misregistrations, and reconstructing a first reconstructed image based on the subtraction frames respectively obtained at the plurality of angles.

* * * * *